US012609297B2

(12) United States Patent
Choi et al.

(10) Patent No.: US 12,609,297 B2
(45) Date of Patent: Apr. 21, 2026

(54) LITHIUM BATTERY

(71) Applicant: SAMSUNG SDI CO., LTD., Yongin-si (KR)

(72) Inventors: Sunjoo Choi, Yongin-si (KR); Yunhee Kim, Yongin-si (KR); Sujeong Koh, Yongin-si (KR); Seungtae Lee, Yongin-si (KR); Siyoung Cha, Yongin-si (KR); Miyoung Son, Yongin-si (KR); Minju Lee, Yongin-si (KR); Myungheui Woo, Yongin-si (KR); Jinhyeok Lim, Yongin-si (KR); Jinah Seo, Yongin-si (KR); Harim Lee, Yongin-si (KR); Erang Cho, Yongin-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 810 days.

(21) Appl. No.: 17/887,613

(22) Filed: Aug. 15, 2022

(65) Prior Publication Data

US 2022/0407055 A1 Dec. 22, 2022

Related U.S. Application Data

(63) Continuation-in-part of application No. 16/135,301, filed on Sep. 19, 2018, now Pat. No. 11,637,322, which is a continuation-in-part of application No. 15/422,873, filed on Feb. 2, 2017, now Pat. No. 11,127,978.

(30) Foreign Application Priority Data

Feb. 12, 2016 (KR) ........................ 10-2016-0016352

(51) Int. Cl.

| | |
|---|---|
| ***H01M 4/36*** | (2006.01) |
| ***H01M 4/131*** | (2010.01) |
| ***H01M 4/505*** | (2010.01) |
| ***H01M 4/525*** | (2010.01) |
| ***H01M 10/0525*** | (2010.01) |
| ***H01M 10/0567*** | (2010.01) |
| ***H01M 10/0568*** | (2010.01) |
| *C07D 327/10* | (2006.01) |
| *H01M 4/02* | (2006.01) |
| *H01M 10/052* | (2010.01) |

(52) U.S. Cl.

CPC ........... *H01M 4/364* (2013.01); *H01M 4/131* (2013.01); *H01M 4/505* (2013.01); *H01M 4/525* (2013.01); *H01M 10/0525* (2013.01); *H01M 10/0567* (2013.01); *H01M 10/0568* (2013.01); *C07D 327/10* (2013.01); *H01M 2004/021* (2013.01); *H01M 2004/028* (2013.01); *H01M 10/052* (2013.01); *H01M 2300/0025* (2013.01)

(58) Field of Classification Search

CPC ...... H01M 4/364; H01M 4/525; H01M 4/505; H01M 4/131; H01M 2004/028; H01M 10/0565; H01M 10/0567; H01M 10/0568; H01M 2300/0025; H01M 10/0525; H01M 2004/021

See application file for complete search history.

(56) References Cited

U.S. PATENT DOCUMENTS

| | | | |
|---|---|---|---|
| 6,180,799 | B1 | 1/2001 | Suri et al. |
| 9,263,766 | B2 | 2/2016 | Makhmut et al. |
| 9,461,334 | B2 | 10/2016 | Ito et al. |
| 2004/0091778 | A1 | 5/2004 | Ozaki et al. |
| 2006/0141361 | A1 | 6/2006 | Yuasa et al. |
| 2010/0075229 | A1 | 3/2010 | Atsuki et al. |
| 2010/0119952 | A1 | 5/2010 | Lee et al. |
| 2010/0297510 | A1 | 11/2010 | Kim et al. |
| 2013/0048461 | A1 | 2/2013 | Pardee et al. |
| 2013/0337326 | A1 | 12/2013 | Mun et al. |

(Continued)

FOREIGN PATENT DOCUMENTS

| | | | |
|---|---|---|---|
| CN | 101202353 | A | 6/2008 |
| CN | 101212065 | A | 7/2008 |

(Continued)

OTHER PUBLICATIONS

Chinese Office action received in copending application No. 201910360743.2 dated Dec. 5, 2022.

(Continued)

*Primary Examiner* — Laura Weiner

(74) *Attorney, Agent, or Firm* — Lee IP Law, P.C.

(57) ABSTRACT

A lithium battery includes a cathode including a cathode active material; an anode including an anode active material; and an organic electrolytic solution between the cathode and the anode, wherein the cathode active material includes a first lithium transition metal oxide and a second lithium transition metal oxide, the first lithium transition metal oxide and the second lithium transition metal oxide have different particle diameters, the second lithium transition metal oxide includes primary particles having a particle diameter of about 1 μm or more, and the organic electrolytic solution includes a first lithium salt, an organic solvent, and a bicyclic sulfate-based compound represented by Formula 1 below:

<Formula 1>

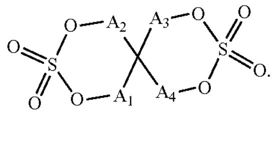

14 Claims, 4 Drawing Sheets

(56) References Cited

U.S. PATENT DOCUMENTS

| | | | |
|---|---|---|---|
| 2014/0342246 | A1 | 11/2014 | Kim |
| 2015/0086861 | A1 | 3/2015 | Makhmut et al. |
| 2015/0140446 | A1 | 5/2015 | Li |
| 2015/0171476 | A1 | 6/2015 | Onozaki et al. |
| 2015/0280282 | A1 | 10/2015 | Nishie et al. |
| 2015/0311504 | A1 | 10/2015 | Hong et al. |
| 2015/0380770 | A1 | 12/2015 | Min |
| 2016/0028115 | A1 | 1/2016 | Kim et al. |
| 2016/0049656 | A1 | 2/2016 | Laicer et al. |
| 2016/0211553 | A1 | 7/2016 | Ito et al. |
| 2016/0254572 | A1 | 9/2016 | Yu et al. |
| 2016/0359196 | A1 | 12/2016 | Kim et al. |
| 2017/0047579 | A1 | 2/2017 | Suehiro et al. |
| 2017/0210855 | A1 | 7/2017 | Wang et al. |
| 2017/0237126 | A1 | 8/2017 | Son et al. |
| 2017/0271715 | A1 | 9/2017 | Kim et al. |
| 2018/0248220 | A1 | 8/2018 | Manabe et al. |
| 2019/0067741 | A1 | 2/2019 | Kim et al. |
| 2019/0198925 | A1 | 6/2019 | Lee et al. |
| 2021/0184202 | A1 | 6/2021 | Salem et al. |

FOREIGN PATENT DOCUMENTS

| | | | |
|---|---|---|---|
| CN | 102237513 | A | 11/2011 |
| CN | 102324568 | A | 1/2012 |
| CN | 102659091 | A | 9/2012 |
| CN | 103515584 | A | 1/2014 |
| CN | 104157901 | A | 11/2014 |
| CN | 104466246 | A | 3/2015 |
| CN | 104718658 | A | 6/2015 |
| CN | 104810551 | A | 7/2015 |
| CN | 104916867 | A | 9/2015 |
| CN | 105428701 | A | 3/2016 |
| CN | 105655564 | A | 6/2016 |
| CN | 106252710 | A | 12/2016 |
| CN | 106463710 | A | 2/2017 |
| CN | 106571468 | A | 4/2017 |
| CN | 107086324 | A | 8/2017 |
| CN | 107528044 | | 12/2017 |
| CN | 107611479 | A | 1/2018 |
| CN | 107925125 | A | 4/2018 |
| EP | 2 913 880 | A1 | 9/2015 |
| JP | 05-290844 | A | 11/1993 |
| JP | 2000-021442 | A | 1/2000 |
| JP | 2007-258103 | A | 10/2007 |
| JP | 2017-117748 | A | 6/2017 |
| JP | 2017-514290 | A | 6/2017 |
| JP | 2017-208246 | A | 11/2017 |
| KR | 10-2001-0095509 | A | 11/2001 |
| KR | 10-2010-0056580 | A | 5/2010 |
| KR | 10-2015-0033445 | A | 4/2015 |
| KR | 10-2015-0048080 | A | 5/2015 |
| KR | 10-2016-0038735 | A | 7/2016 |
| KR | 10-2016-0144123 | A | 12/2016 |
| KR | 10-2017-0039369 | A | 4/2017 |
| KR | 20170094966 | A | 8/2017 |
| KR | 10-2018-0083272 | A | 7/2018 |
| WO | WO 2014/068805 | A1 | 5/2014 |
| WO | WO 2014/195407 | | 12/2014 |
| WO | WO 2014/196177 | A1 | 12/2014 |
| WO | WO 2015/046475 | A1 | 4/2015 |
| WO | WO 2015/060697 | A1 | 4/2015 |
| WO | WO 2015/129166 | A1 | 9/2015 |
| WO | WO 2017-010820 | A | 1/2017 |
| WO | WO 2017-061102 | A | 4/2017 |
| WO | WO 2018-097523 | A | 5/2018 |

OTHER PUBLICATIONS

Chinese Office action received in copending application No. 201910375503.X dated Dec. 5, 2022.

Chinese Office action received in copending application No. 201910375148.6 dated Dec. 5, 2022.

Chinese Reexamination Notification dated Aug. 24, 2023.

Chinese Grant Publication dated Jul. 11, 2023.

New Synthetic Routes Towards Hydrophilic Phosphanes, Gulyás, H., University of Veszprém.

Synthesis of sulfated mono- and ditertiary phosphines, complex chemistry and catalysis, Gulyás, H., Canadian Journal of Chemistry, 2001, 79(5-6), pp. 1040-1048.

Moon-Ho Choiet al., "Effect of Lithium in Transmition Metal Layers of Ni-Rich Cathode . . . " Journal of the Electrochemical Society, 262 (12),2015.

Yu-Han Li et al., "Electrochemical characterization of a branched oligomer as a high-temperature and long-cycle-life additive for lithium-ion batteries", Electrochimica Acta, 85, 72-77, Aug. 25, 2012.

Chinese Notice of Allowance mailed Jul. 11, 2022 for corresponding CN Patent Application No. 201910359895.0.

Chinese Notice of Allowance mailed Jun. 6, 2022 for corresponding CN Patent Application No. 201910375226.2.

Chinese Office action dated Jul. 11, 2022 for corresponding CN 201910360134.

Chinese Office action dated Jul. 11, 2022 for corresponding CN 201910375503.

Chinese Office action dated Jul. 12, 2022 for corresponding CN 201910360569.

Chinese Office action dated Jul. 8, 2022 for corresponding CN 201910360743.

Chinese Office action dated Mar. 2, 2022.

Chinese Office action dated Nov. 13, 2020.

Chinese Office action mailed Dec. 2, 2021 for corresponding member CN Patent Application No. 201910360134.7.

Chinese Office action mailed Dec. 2, 2021 for corresponding member CN Patent Application No. 201910375148.6.

Chinese Office action mailed Dec. 29, 2021 for corresponding member CN Patent Application No. 201910375226.2.

Chinese Office action mailed Dec. 30, 2021 for corresponding member CN Patent Application No. 201910360743.2.

Chinese Office action mailed Jan. 4, 2022 for corresponding member CN Patent Application No. 201910360569.1.

Chinese Office Action mailed Jul. 7, 2022 for corresponding CN Patent Application No. 201910375148.6.

Chinese Office action mailed Nov. 30, 2021 for corresponding member CN Patent Application No. 201910359895.0.

Extended European Search Report issued by the European Patent Office on Mar. 17, 2017, in the examination of the European Patent Application No. 17 155 590.7.

Korean Office action dated Apr. 29, 2022 for corresponding KR 10-2019-114961.

Korean Office action dated Apr. 29, 2022 for corresponding KR 10-2019-114965.

Korean Office action dated Apr. 29, 2022 for corresponding KR 10-2019-114963.

Korean Office action dated Apr. 6, 2022.

Korean Office action dated Jun. 21, 2022 for corresponding KR 10-2019-114957.

Korean Office action dated Jun. 21, 2022 for corresponding KR 10-2019-114966.

Korean Office Action mailed Mar. 20, 2019.

Korean Registration Determination Certificate dated Jun. 5, 2020.

USPTO Office action in U.S. Appl. No. 16/135,396 on Oct. 23, 2020.

USPTO Office action in U.S. Appl. No. 16/135,342 on Oct. 23, 2020.

USPTO Office action in U.S. Appl. No. 16/135,403 on Oct. 19, 2020.

USPTO Office action in U.S. Appl. No. 16/135,420 mailed Nov. 13, 2020.

USPTO Office action issued in U.S. Appl. No. 16/135,342 dated Jul. 9, 2021.

USPTO Office action issued in U.S. Appl. No. 16/135,342 dated Mar. 3, 2021.

USPTO Office action issued in U.S. Appl. No. 16/135,349 dated Apr. 15, 2021.

USPTO Office action issued in U.S. Appl. No. 16/135,395 dated Mar. 3, 2021.

(56) References Cited

OTHER PUBLICATIONS

USPTO Office action issued in U.S. Appl. No. 16/135,403 dated Mar. 4, 2021.
USPTO Office Action issued on Apr. 30, 2019, in copending U.S. Appl. No. 15/422,873.
USPTO Office action mailed Apr. 17, 2020 for parent U.S. Appl. No. 15/422,873.
USPTO Office action received in co pending U.S. Appl. No. 16/135,395 dated Jul. 22, 2021.
USPTO Office action received in copending U.S. Appl. No. 16/135,349 dated Jan. 7, 2021.
USPTO Office action received in U.S. Appl. No. 15/422,873 dated Aug. 27, 2020.
Chinese Office action dated Mar. 7, 2023.
U.S. Appl. No. 17/887,591, filed Aug. 15, 2022.
U.S. Appl. No. 17/887,597, filed Aug. 15, 2022.
U.S. Appl. No. 17/887,621, filed Aug. 15, 2022.
U.S. Appl. No. 17/887,636, filed Aug. 15, 2022.
Decision on Reexamination dated Oct. 31, 2023, of the corresponding CN Patent Application No. 201910360743.2.
Chinese Office action dated Feb. 28, 2023.
J. Yan, et al. "Recent Progress in Li-rich Layered Oxides, etc . . . " RSC Advances, Dec. 11, 2014.
U.S. Office Action received in co-pending U.S. Appl. No. 17/887,597, dated Jul. 31, 2025.
U.S. Office Action received in co-pending U.S. Appl. No. 17/887,591, dated Jul. 7, 2025.
U.S. Office Action received in co-pending U.S. Appl. No. 17/887,636, dated Aug. 13, 2025.

LITHIUM BATTERY

CROSS-REFERENCE TO RELATED APPLICATION

This application is a continuation-in-part of U.S. Patent Application Ser. No. 16/135,301 filed Sep. 19, 2018, which issued as U.S. Pat. No. 11,637,322 on Apr. 25, 2023, which is a continuation-in-part of U.S. patent application Ser. No. 15/422,873, filed on Feb. 2, 2017, which issued as U.S. Pat. No. 11,127,978 on Sep. 21, 2021, both entitled "Lithium Battery" which are hereby incorporated by reference in their entirety. Korean Patent Application No. 10-2016-0016352, filed on Feb. 12, 2016, in the Korean Intellectual Property Office, and entitled: "Lithium Battery," is incorporated by reference herein in its entirety.

BACKGROUND

1. Field

Embodiments relate to lithium batteries.

2. Description of the Related Art

Lithium batteries are used as driving power sources for portable electronic devices, including video cameras, mobile phones, notebook computers, and the like. Lithium secondary batteries are rechargeable at high rates and have an energy density per unit weight that is at least three times as large as that of existing lead storage batteries, nickel-cadmium batteries, nickel-hydrogen batteries, or nickel-zinc batteries.

SUMMARY

Embodiments are directed to a lithium battery including a cathode including a cathode active material, an anode including an anode active material, and an organic electrolytic solution between the cathode and the anode. The cathode active material includes a first lithium transition metal oxide and a second lithium transition metal oxide. The first lithium transition metal oxide and the second lithium transition metal oxide may have different particle diameters. The second lithium transition metal oxide may include primary particles having a particle diameter of about 1 μm or more. The organic electrolytic solution includes a first lithium salt, an organic solvent, and a bicyclic sulfate-based compound represented by Formula 1 below:

<Formula 1>

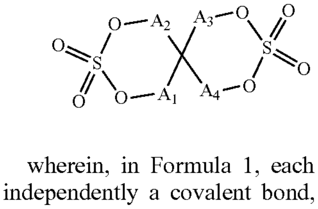

wherein, in Formula 1, each of $A_1$, $A_2$, $A_3$, and $A_4$ is independently a covalent bond, a substituted or unsubstituted $C_1$-$C_5$ alkylene group, a carbonyl group, or a sulfinyl group, wherein both $A_1$ and $A_2$ are not a covalent bond and both $A_3$ and $A_4$ are not a covalent bond.

At least one of $A_1$, $A_2$, $A_3$, and $A_4$ may be an unsubstituted or substituted $C_1$-$C_5$ alkylene group, wherein a substituent of the substituted $C_1$-$C_5$ alkylene group is at least one selected from a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, a halogen-substituted or unsubstituted $C_2$-$C_{40}$ heteroaryl group, or a polar functional group having at least one heteroatom.

At least one of $A_1$, $A_2$, $A_3$, and $A_4$ may be an unsubstituted or substituted $C_1$-$C_5$ alkylene group, wherein a substituent of the substituted $C_1$-$C_5$ alkylene group is a halogen, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

The substituted $C_1$-$C_5$ alkylene group may be substituted with a polar functional group including at least one heteroatom, wherein the polar functional group is —F, —Cl, —Br, —I, —C(═O)OR$^{16}$, —OR$^{16}$, —OC(═O)OR$^{16}$, —R$^{15}$OC(═O)OR$^{16}$, —C(═O)R$^{16}$, —R$^{15}$C(═O)R$^{16}$, —OC(═O)R$^{16}$, —R$^{15}$OC(═O)R$^{16}$, —C(═O)—O—C(═O)R$^{16}$, —R$^{15}$C(═O)—O—C(═O)R$^{16}$, —SR$^{16}$, —R$^{15}$SR$^{16}$, —SSR$^{16}$, —R$^{15}$SSR$^{16}$, —S(═O)R$^{16}$, —R$^{15}$S(═O)R$^{16}$, —R$^{15}$C(═S)R$^{16}$, —R$^{15}$C(═S)SR$^{16}$, —R$^{15}$SO$_3$R$^{16}$, —SO$_3$R$^{16}$, —NNC(═S)R$^{16}$, —R$^{15}$NNC(═S)R$^{16}$, —R$^{15}$N═C═S, —NCO, —R$^{15}$—NCO, —NO$_2$, —R$^{15}$NO$_2$, —R$^{15}$SO$_2$R$^{16}$, —SO$_2$R$^{16}$,

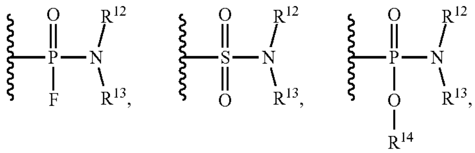

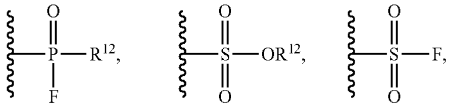

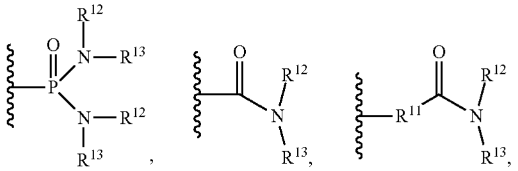

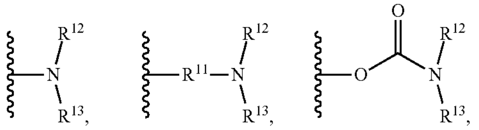

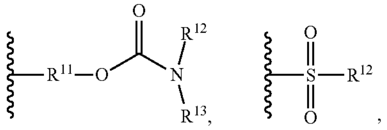

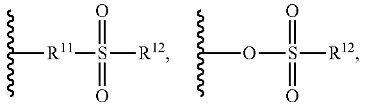

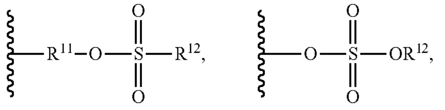

-continued

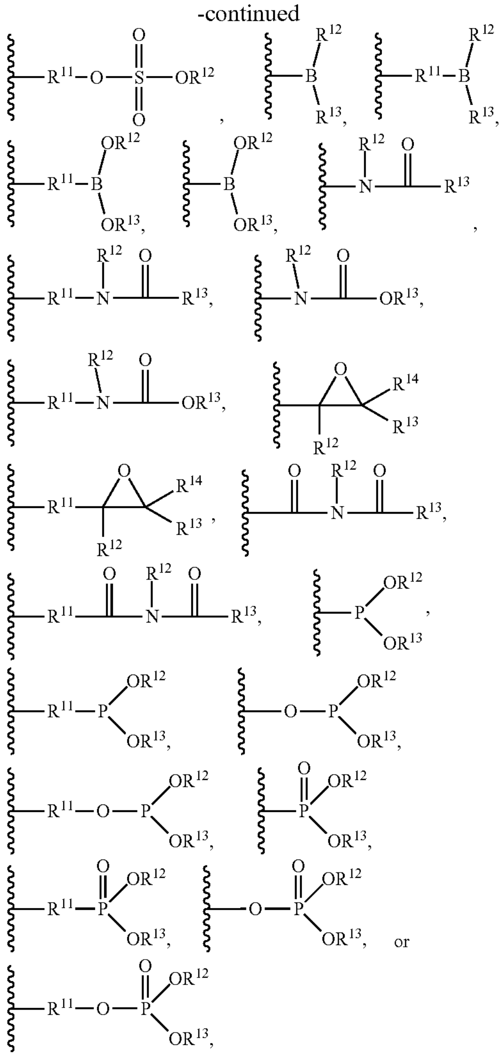

wherein, in the formulae above, each of $R^{11}$ and $R^{15}$ is independently a halogen-substituted or unsubstituted $C_1$-$C_{20}$ alkylene group, a halogen-substituted or unsubstituted $C_2$-$C_{20}$ alkenylene group, a halogen-substituted or unsubstituted $C_2$-$C_{20}$ alkynylene group, a halogen-substituted or unsubstituted $C_3$-$C_{12}$ cycloalkylene group, a halogen-substituted or unsubstituted $C_6$-$C_{40}$ arylene group, a halogen-substituted or unsubstituted $C_2$-$C_{40}$ heteroarylene group, a halogen-substituted or unsubstituted $C_7$-$C_{15}$ alkylarylene group, or a halogen-substituted or unsubstituted $C_7$-$C_{15}$ aralkylene group; and each of $R^{12}$, $R^{13}$, $R^{14}$ and $R^{16}$ is independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_2$ cycloalkyl group, a halogen-substituted or unsubstituted $C_6$-$C_{40}$ aryl group, a halogen-substituted or unsubstituted $C_2$-$C_{40}$ heteroaryl group, a halogen-substituted or unsubstituted $C_7$-$C_{15}$ alkylaryl group, a halogen-substituted or unsubstituted $C_7$-$C_{15}$ trialkylsilyl group, or a halogen-substituted or unsubstituted $C_7$-$C_{15}$ aralkyl group.

The bicyclic sulfate-based compound may be represented by Formula 2 or 3:

<Formula 2>

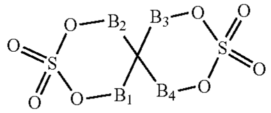

<Formula 3>

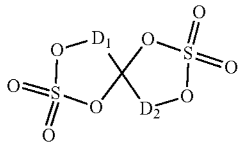

wherein, in Formulae 2 and 3, each of $B_1$, $B_2$, $B_3$, $B_4$, $D_1$, and $D_2$ is independently —$C(E_1)(E_2)$-, a carbonyl group, or a sulfinyl group; and each of $E_1$ and $E_2$ is independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, or a halogen-substituted or unsubstituted $C_2$-$C_{40}$ heteroaryl group.

Each of $E_1$ and $E_2$ may be independently hydrogen, a halogen, a halogen-substituted or unsubstituted $C_1$-$C_{10}$ alkyl group, a halogen-substituted or unsubstituted $C_6$-$C_{40}$ aryl group, or a halogen-substituted or unsubstituted $C_2$-$C_{40}$ heteroaryl group.

Each of $E_1$ and $E_2$ may be independently hydrogen, fluorine (F), chlorine (Cl), bromine (Br), iodine (I), a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

The bicyclic sulfate-based compound may be represented by Formula 4 or 5:

<Formula 4>

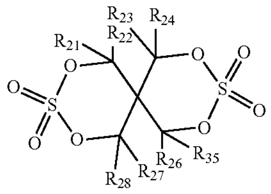

<Formula 5>

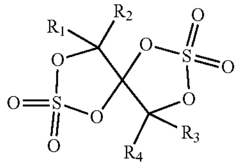

wherein, in Formulae 4 and 5, each of $R_1$, $R_2$, $R_3$, $R_4$, $R_{21}$, $R_{22}$, $R_{23}$, $R_{24}$, $R_{25}$, $R_{26}$, $R_{27}$, and $R_{28}$ is independently hydrogen, a halogen, a halogen-substituted or unsubstituted $C_1$-$C_{20}$ alkyl group, a halogen-substituted or unsubstituted $C_6$-$C_{40}$ aryl group, or a halogen-substituted or unsubstituted $C_2$-$C_{40}$ heteroaryl group.

Each of $R_1$, $R_2$, $R_3$, $R_4$, $R_{21}$, $R_{22}$, $R_{23}$, $R_{24}$, $R_{25}$, $R_{26}$, $R_{27}$, and $R_{28}$ may be independently hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

The bicyclic sulfate-based compound may be represented by one of Formulae 6 to 17 below:

<Formula 6>

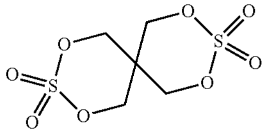

<Formula 7>

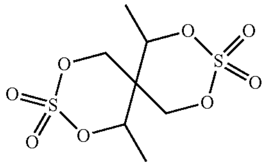

<Formula 8>

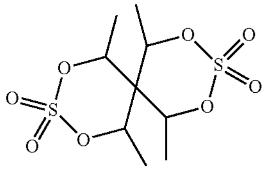

<Formula 9>

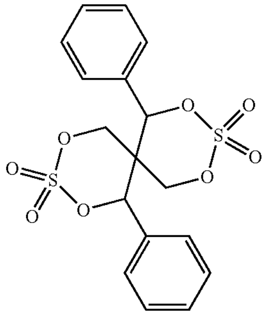

<Formula 10>

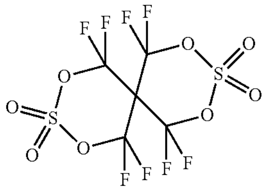

<Formula 11>

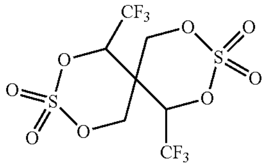

<Formula 12>

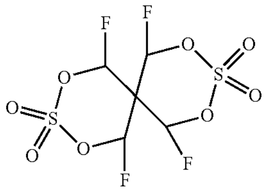

-continued

<Formula 13>

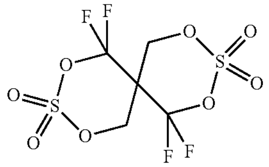

<Formula 14>

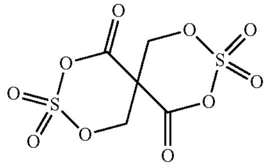

<Formula 15>

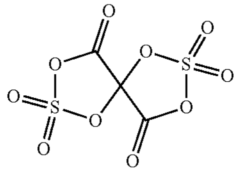

<Formula 16>

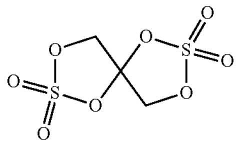

<Formula 17>

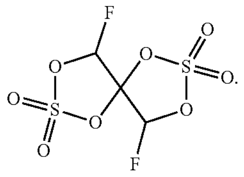

An amount of the bicyclic sulfate-based compound may be from about 0.4 wt % to about 5 wt % based on a total weight of the organic electrolytic solution.

An amount of the bicyclic sulfate-based compound may be from about 0.4 wt % to about 3 wt % based on a total weight of the organic electrolytic solution.

The first lithium salt in the organic electrolytic solution may include at least one selected from $LiPF_6$, $LiBF_4$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlCl_4$, $LiN(C_xF_{2x+1}SO_2)(C_yF_{2y+1}SO_2)$ where $2 \leq x \leq 20$ and $2 \leq y \leq 20$, LiCl, and LiI.

The organic electrolytic solution may further include a cyclic carbonate compound, wherein the cyclic carbonate compound is selected from vinylene carbonate (VC), VC substituted with a halogen, a cyano (CN) group, or a nitro group ($NO_2$), vinylethylene carbonate (VEC), VEC substituted with a halogen, CN, or $NO_2$, fluoroethylene carbonate (FEC), or FEC substituted with a halogen, CN, or $NO_2$.

An amount of the cyclic carbonate compound may be from about 0.01 wt % to about 5 wt % based on a total weight of the organic electrolytic solution.

The organic electrolytic solution may further include a second lithium salt different from the first lithium salt and represented by one of Formulae 18 to 25 below:

<Formula 18>

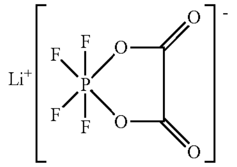

<Formula 19>

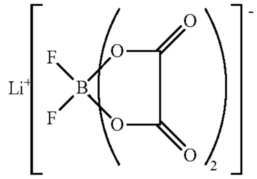

<Formula 20>

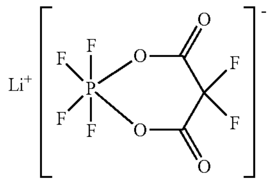

<Formula 21>

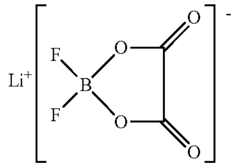

<Formula 22>

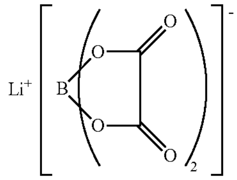

<Formula 23>

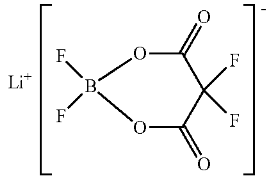

<Formula 24>

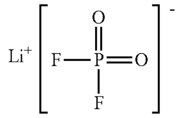

<Formula 25>

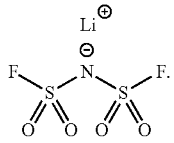

An amount of the second lithium salt may be from about 0.1 wt % to about 5 wt % based on a total weight of the organic electrolytic solution.

The first lithium transition metal oxide and the second lithium transition metal oxide may have a bimodal particle size distribution in particle size distribution.

A particle diameter ratio of the first lithium transition metal oxide to the second lithium transition metal oxide may be from about 3:1 to about 40:1.

The first lithium transition metal oxide may have a particle diameter of greater than about 8 μm to about 30 μm, and the second lithium transition metal oxide may have a particle diameter of about 1 μm to less than about 8 μm.

A weight ratio of the first lithium transition metal oxide to the second lithium transition metal oxide is from about 78:22 to about 60:40.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
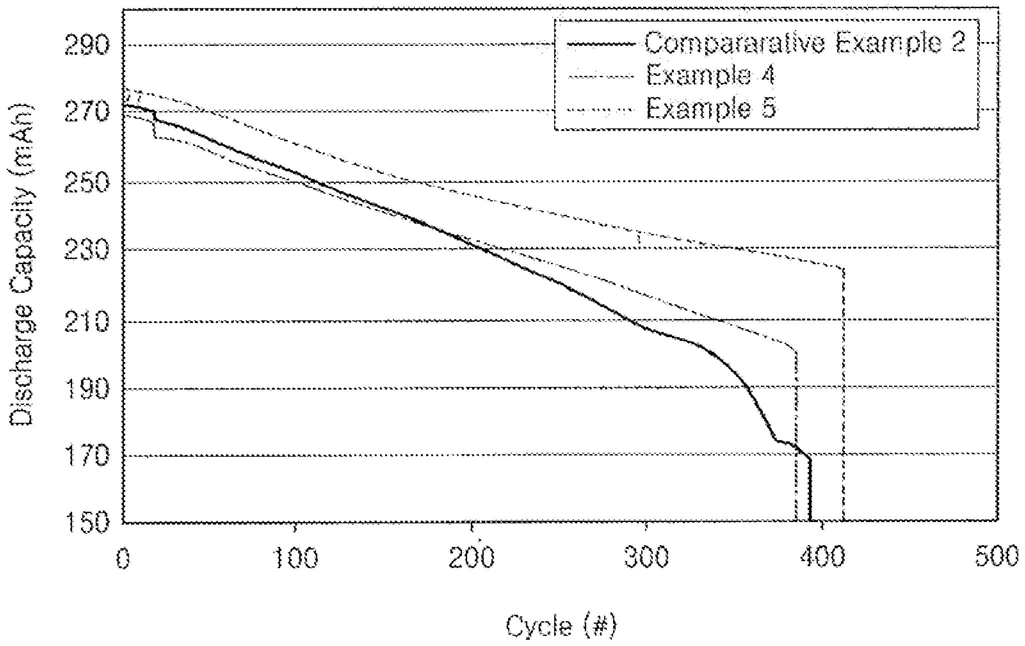
FIG. 1 illustrates a graph showing discharge capacities at room temperature of lithium batteries manufactured according to Examples 4 and 5 and Comparative Example 2.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

Hereinafter, a lithium battery according to example embodiments will be described in more detail.

A lithium battery according to an embodiment may include a cathode including a cathode active material, an anode including an anode active material, and an organic electrolytic solution between the cathode and the anode. The cathode active material may include a first lithium transition metal oxide and a second lithium transition metal oxide, and the first lithium transition metal oxide and the second lithium transition metal oxide may have different particle diameters. The second lithium transition metal oxide may include primary particles having a particle diameter of about 1 μm or more. The organic electrolytic solution may include a first lithium salt; an organic solvent; and a bicyclic sulfate-based compound represented by Formula 1 below:

<Formula 1>

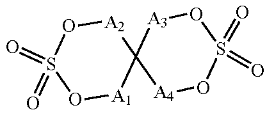

wherein, in Formula 1, each of $A_1$, $A_2$, $A_3$, and $A_4$ is independently a covalent bond, a substituted or unsubstituted $C_1$-$C_5$ alkylene group, a carbonyl group, or a sulfinyl group, in which both $A_1$ and $A_2$ are not a covalent bond and both $A_3$ and $A_4$ are not a covalent bond.

The organic electrolytic solution as an additive for a lithium battery, including the bicyclic sulfate-based compound, may enhance battery performance, such as high-temperature characteristics, lifespan characteristics, or the like.

In addition, when the cathode active material in the cathode includes a nickel-containing layered lithium transition metal oxide and the content of nickel in the lithium transition metal oxide is about 60 mol % or more with respect to the total number of moles of transition metals, the lithium battery may exhibit further enhanced lifespan characteristics and further enhanced high-temperature stability.

In addition, the cathode active material may include a first lithium transition metal oxide and a second lithium transition metal oxide, the first lithium transition metal oxide and the second lithium transition metal oxide may have different particle diameters, the second lithium transition metal oxide may include primary particles, i.e., one-body particles, having a particle diameter of about 1 μm or more, and, when the organic electrolytic solution includes the compound of Formula 1, the lithium battery may exhibit enhanced cycle characteristics. The primary particles having a particle diameter of about 1 μm or more may be, for example, single crystal particles. In some other lithium batteries, one-body particles have a reduced specific surface area, and cracks therein during charging/discharging are suppressed, resulting in suppressed side reactions with an electrolytic solution, but the diffusion of lithium into primary particles may not be easy, thus increasing internal resistance. During charging/discharging of the lithium battery, a high-resistance solid electrolyte interface (SEI) layer may be further formed on surfaces of primary particles, and thus the internal resistance of the primary particles may be further increased. In contrast, in the lithium battery according to an embodiment, the organic electrolytic solution may include the compound of Formula 1, and thus, an increase in resistance of a SEI layer formed on surfaces of one-body particles may be suppressed, resulting in suppressed increase in internal resistance of the lithium battery.

The bicyclic sulfate-based compound may have a structure in which two sulfate rings are linked to each other in a spiro form.

Without being bound to any particular theory and for better understanding, a reason for which the performance of a lithium battery is improved by addition of the bicyclic sulfate-based compound to the electrolytic solution will now be described in further detail.

When a bicyclic sulfate-based compound is included in the electrolytic solution, a sulfate ester group of the bicyclic sulfate-based compound may be reduced by itself by accepting electrons from a surface of an anode during charging, or may react with a previously -reduced polar solvent molecule, thereby affecting characteristics of an SEI layer formed at the surface of the anode. For example, the bicyclic sulfate-based compound including the sulfate ester group may more easily accept electrons from an anode, as compared to polar solvents. For example, the bicyclic sulfate-based compound may be reduced at a lower voltage than a polar solvent before the polar solvent is reduced.

For example, the bicyclic sulfate-based compound includes a sulfate ester group, and thus may be more easily reduced and/or decomposed into radicals and/or ions during charging. Consequently, the radicals and/or ions may bind with lithium ions to form an appropriate SEI layer on an anode, thereby preventing formation of a product obtained by further decomposition of a solvent. The bicyclic sulfate-based compound may form a covalent bond with, for example, a carbonaceous anode itself or a variety of functional groups on the surface of the carbonaceous anode, or may be adsorbed onto the surface of an electrode. A modified SEI layer with improved stability, formed by such binding and/or adsorption, may be more durable even after charging and discharging for a long time period, as compared to an SEI layer formed from only an organic solvent. The durable modified SEI layer may in turn more effectively block co-intercalation of the organic solvent solvating lithium ions during intercalation of the lithium ions into an electrode. Accordingly, the modified SEI layer may more effectively block direct contact between the organic solvent and an anode to further improve reversibility of intercalation/deintercalation of lithium ions, resulting in an increase in discharge capacity and improvement of lifespan characteristics of the battery fabricated.

Also, due to the inclusion of the sulfate ester group, the bicyclic sulfate-based compound may be coordinated on a surface of a cathode, thereby affecting characteristics of a protection layer formed on the surface of the cathode. For example, the sulfate ester group may be coordinated to transition metal ions of a cathode active material to form a complex. This complex may form a modified protection layer with improved stability that is more durable even after charging and discharging for a long time period than a protection layer formed from only the organic solvent. In addition, the durable modified protection layer may more effectively block co-intercalation of the organic solvent solvating lithium ions during intercalation of the lithium ions into an electrode. Accordingly, the modified protection layer may more effectively block direct contact between the organic solvent and the cathode to further improve the reversibility of intercalation/deintercalation of lithium ions, resulting in increased stability and improved lifespan characteristics of the battery fabricated.

In addition, the bicyclic sulfate-based compound has a structure in which a plurality of rings are linked in a spiro form and thus has a relatively larger molecular weight than that of a general sulfate-based compound and accordingly, may be thermally stable.

For example, the bicyclic sulfate-based compound may form an SEI layer at a surface of an anode or a protection layer at a surface of a cathode and may exhibit enhanced lifespan characteristics of the lithium battery fabricated at a high temperature due to the improved thermal stability.

In the bicyclic sulfate-based compound of Formula 1 above included in the organic electrolytic solution, at least one of $A_1$, $A_2$, $A_3$, and $A_4$ may be an unsubstituted or substituted $C_1$-$C_5$ alkylene group, and a substituent of the substituted $C_1$-$C_5$ alkylene group may be a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, a halogen-substituted or unsubstituted $C_2$-$C_{40}$ heteroaryl group, or a polar functional group having at least one heteroatom.

For example, at least one of $A_1$, $A_2$, $A_3$, and $A_4$ may be an unsubstituted or substituted $C_1$-$C_5$ alkylene group, and a substituent of the substituted $C_1$-$C_5$ alkylene group may be a halogen, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group. For example, the substituent of the substituted $C_1$-$C_5$ alkylene group may be a suitable substituent available for alkylene groups used in the art.

In some implementations, in the bicyclic sulfate-based compound of Formula 1 above, the substituent of the substituted $C_1$-$C_5$ alkylene group may be a polar functional group having a heteroatom. The heteroatom of the polar functional group may be at least one selected from oxygen, nitrogen, phosphorus, sulfur, silicon, and boron.

For example, the polar functional group having a heteroatom may be —F, —Cl, —Br, —I, $—C(=O)OR^{16}$, $—OR^{16}$, $—OC(=O)OR^{16}$, $—R^{15}OC(=O)OR^{16}$, $—C(=O)R^{16}$, $—R^{15}C(=O)R^{16}$, $—OC(=O)R^{16}$, $—R^{15}OC(=O)R^{16}$, $—C(=O)—O—C(=O)R^{16}$, $—R^{15}C(=O)—O—C(=O)R^{16}$, $—SR^{16}$, $—R^{15}SR^{16}$, $—SSR^{16}$, $—R^{15}SSR^{16}$, $—S(=O)R^{16}$, $—R^{15}S(=O)R^{16}$, $—R^{15}C(=S)R^{16}$, $—R^{15}C(=S)SR^{16}$, $—R^{15}SO_3R^{16}$, $—SO_3R^{16}$, $—NNC(=S)R^{16}$, $—R^{15}NNC(=S)R^{16}$, $—R^{15}N=C=S$, —NCO, $—R^{15}—NCO$, $—NO_2$, $—R^{15}NO_2$, $—R^{15}SO_2R^{16}$, $—SO_2R^{16}$,

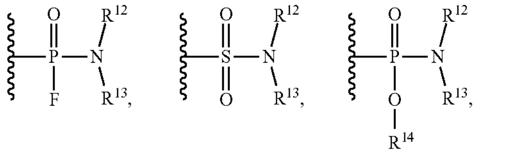

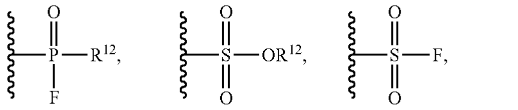

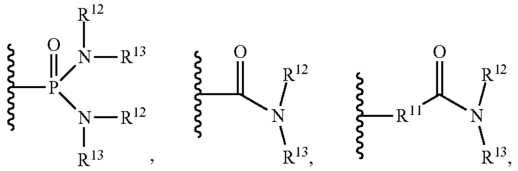

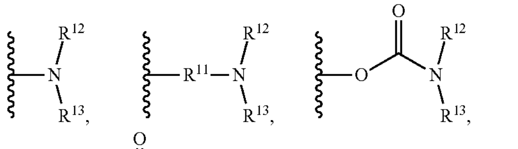

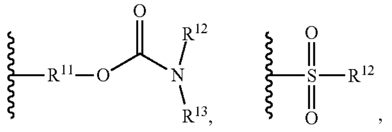

-continued

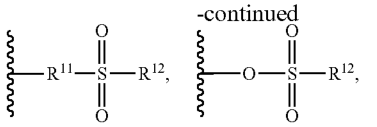

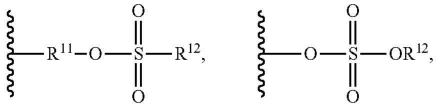

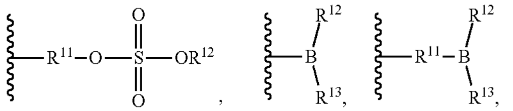

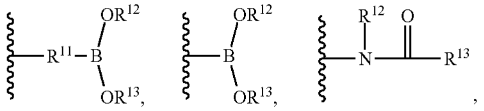

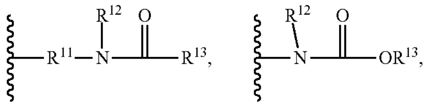

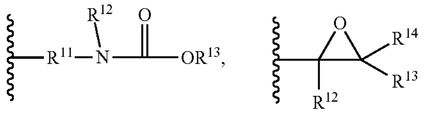

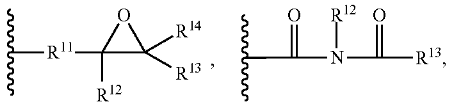

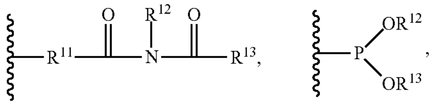

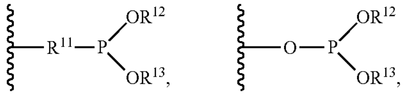

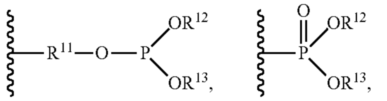

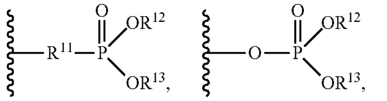

or

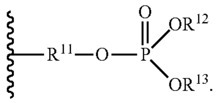

In the above formulae, each of $R^{11}$ and $R^{15}$ may be independently a halogen-substituted or unsubstituted $C_1$-$C_{20}$ alkylene group, a halogen-substituted or unsubstituted $C_2$-$C_{20}$ alkenylene group, a halogen-substituted or unsubstituted $C_2$-$C_{20}$ alkynylene group, a halogen-substituted or unsubstituted $C_3$-$C_{12}$ cycloalkylene group, a halogen-substituted or unsubstituted $C_6$-$C_{40}$ arylene group, a halogen-substituted or unsubstituted $C_2$-$C_{40}$ heteroarylene group, a halogen-substituted or unsubstituted $C_7$-$C_{15}$ alkylarylene group, or a halogen-substituted or unsubstituted $C_7$-$C_{15}$ aralkylene group. Each of $R^{12}$, $R^{13}$, $R^{14}$ and $R^{16}$ may be independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_2$ cycloalkyl group, a halogen-substituted or unsubstituted $C_6$-$C_{40}$ aryl group, a halogen-substituted or unsubstituted $C_2$-$C_{40}$ heteroaryl group, a halogen-substituted or unsubstituted $C_7$-$C_{15}$ alkylaryl group, a halogen-substituted or unsubstituted $C_7$-$C_{15}$ trialkylsilyl group, or a halogen-substituted or unsubstituted $C_7$-$C_{15}$ aralkyl group.

For example, in the polar functional group having a heteroatom, a halogen substituent of the alkyl group, the alkenyl group, the alkynyl group, the cycloalkyl group, the aryl group, the heteroaryl group, the alkylaryl group, the trialkylsilyl group, or the aralkyl group may be fluorine (F).

For example, the bicyclic sulfate-based compound included in the organic electrolytic solution may be represented by Formula 2 or 3:

<Formula 2>

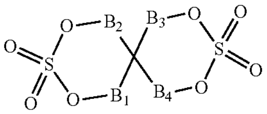

<Formula 3>

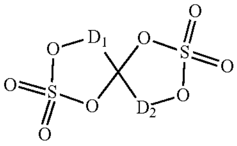

wherein, in Formulae 2 and 3, each of $B_1$, $B_2$, $B_3$, $B_4$, $D_1$, and $D_2$ may be independently —$C(E_1)(E_2)$-, a carbonyl group, or a sulfinyl group. Each of $E_1$ and $E_2$ may be independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, or a halogen-substituted or unsubstituted $C_2$-$C_4$n heteroaryl group.

For example, each of $E_1$ and $E_2$ may be independently hydrogen, a halogen, a halogen-substituted or unsubstituted $C_1$-$C_{10}$ alkyl group, a halogen-substituted or unsubstituted $C_6$-$C_{40}$ aryl group, or a halogen-substituted or unsubstituted $C_2$-$C_{40}$ heteroaryl group.

For example, each of $E_1$ and $E_2$ may be independently hydrogen, F, chlorine (Cl), bromine (Br), iodine (I), a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

For example, each of $E_1$ and $E_2$ may be independently hydrogen, F, a methyl group, an ethyl group, a trifluoromethyl group, a tetrafluoroethyl group, or a phenyl group.

For example, the bicyclic sulfate-based compound may be represented by Formula 4 or 5:

<Formula 4>

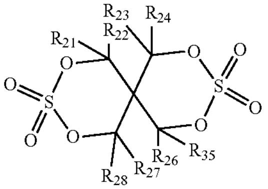

-continued

<Formula 5>

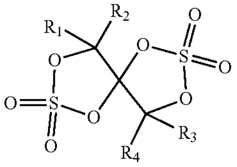

wherein, in Formulae 4 and 5, each of $R_1$, $R_2$, $R_3$, $R_4$, $R_{21}$, $R_{22}$, $R_{23}$, $R_{24}$, $R_{25}$, $R_{26}$, $R_{27}$, and $R_{28}$ may be independently hydrogen, a halogen, a halogen-substituted or unsubstituted $C_1$-$C_{20}$ alkyl group, a halogen-substituted or unsubstituted $C_6$-$C_{40}$ aryl group, or a halogen-substituted or unsubstituted $C_2$-$C_{40}$ heteroaryl group.

For example, in Formulae 4 and 5 above, each of $R_1$, $R_2$, $R_3$, $R_4$, $R_{21}$, $R_{22}$, $R_{23}$, $R_{24}$, $R_{25}$, $R_{26}$, $R_{27}$, and $R_{28}$ may be independently hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrole group, or a pyridine group.

For example, in Formulae 4 and 5 above, each of $R_1$, $R_2$, $R_3$, $R_4$, $R_{21}$, $R_{22}$, $R_{23}$, $R_{24}$, $R_{25}$, $R_{26}$, $R_{27}$, and $R_{28}$ may be independently hydrogen, F, a methyl group, an ethyl group, a propyl group, a trifluoromethyl group, a tetrafluoroethyl group, or a phenyl group.

For example, the bicyclic sulfate-based compound may be represented by one of Formulae 6 to 17:

<Formula 6>

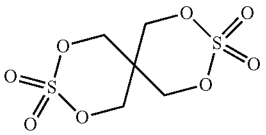

<Formula 7>

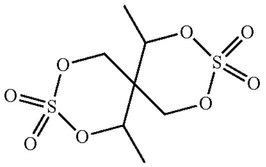

<Formula 8>

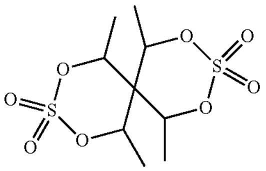

<Formula 9>

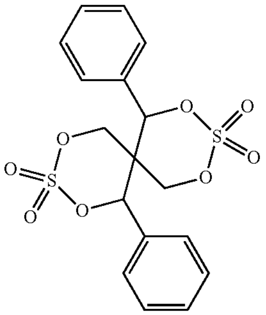

-continued

<Formula 10>

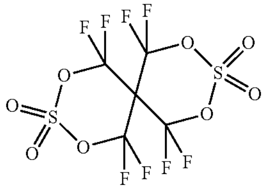

<Formula 11>

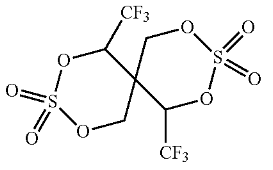

<Formula 12>

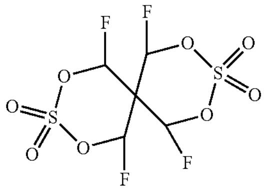

<Formula 13>

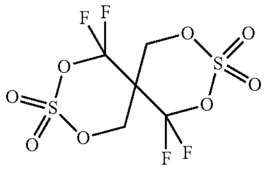

<Formula 14>

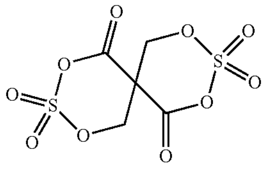

<Formula 15>

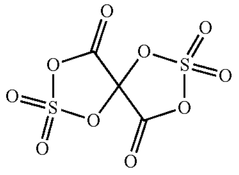

<Formula 16>

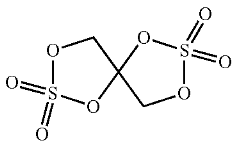

<Formula 17>

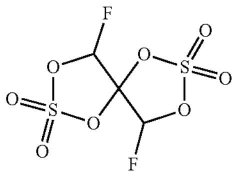

As used herein, a and b of the expression "Ca-Cb" indicates the number of carbon atoms of a particular functional group. For example, the functional group may include a to b carbon atoms. For example, the expression "$C_1$-$C_4$ alkyl group" indicates an alkyl group having 1 to 4 carbon atoms, i.e., $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

A particular radical may be called a mono-radical or a di-radical depending on the context. For example, when a substituent needs two binding sites for binding with the rest of the molecule, the substituent may be understood as a di-radical. For example, a substituent specified as an alkyl group that needs two binding sites may be a di-radical, such as —$CH_2$—, —$CH_2CH_2$—, —$CH_2CH(CH_3)CH_2$—, or the like. The term "alkylene" as used herein indicates that the radical is a di-radical.

The terms "alkyl group" and "alkylene group" as used herein refer to a branched or unbranched aliphatic hydrocarbon group. In an embodiment, the alkyl group may be substituted or unsubstituted. Examples of the alkyl group include a methyl group, an ethyl group, a propyl group, an isopropyl group, a butyl group, an isobutyl group, a tert-butyl group, a pentyl group, a hexyl group, a cyclopropyl group, a cyclopentyl group, a cyclohexyl group, and a cycloheptyl group, each of which may be optionally substituted or unsubstituted. In an embodiment, the alkyl group may have 1 to 6 carbon atoms. For example, a $C_1$-$C_6$ alkyl group may be methyl, ethyl, propyl, isopropyl, butyl, isobutyl, sec-butyl, pentyl, 3-pentyl, hexyl, or the like.

The term "cycloalkyl group" as used herein refers to a fully saturated carbocyclic ring or ring system. For example, the cycloalkyl group may be cyclopropyl, cyclobutyl, cyclopentyl, and cyclohexyl.

The term "alkenyl group" as used herein refers to a hydrocarbon group having 2 to 20 carbon atoms with at least one carbon-carbon double bond. examples of the alkenyl group include an ethenyl group, a 1-propenyl group, a 2-propenyl group, a 2-methyl-1-propenyl group, a 1-butenyl group, a 2-butenyl group, a cyclopropenyl group, a cyclopentenyl group, a cyclohexenyl group, and a cycloheptenyl group. In an embodiment, these alkenyl groups may be substituted or unsubstituted. In an embodiment, the alkenyl group may have 2 to 40 carbon atoms.

The term "alkynyl group" as used herein refers to a hydrocarbon group having 2 to 20 carbon atoms with at least one carbon-carbon triple bond. Examples of the alkynyl group include an ethynyl group, a 1-propynyl group, a 1-butynyl group, and a 2-butynyl group. In an embodiment, these alkynyl groups may be substituted or unsubstituted. In an embodiment, the alkynyl group may have 2 to 40 carbon atoms.

The term "aromatic" as used herein refers to a ring or ring system with a conjugated π electron system, and may refer to a carbocyclic aromatic group (e.g., a phenyl group) and a heterocyclic aromatic group (e.g., pyridine). In this regard, an aromatic ring system as a whole may include a monocyclic ring or a fused polycyclic ring (i.e., a ring that shares adjacent atom pairs).

The term "aryl group" as used herein refers to an aromatic ring or ring system (i.e., a ring fused from at least two rings that shares two adjacent carbon atoms) having only carbon atoms in its backbone. When the aryl group is a ring system, each ring in the ring system is aromatic. Examples of the aryl group include a phenyl group, a biphenyl group, a naphthyl group, a phenanthrenyl group, and naphthacenyl group. These aryl groups may be substituted or unsubstituted.

The term "heteroaryl group" as used herein refers to an aromatic ring system with one ring or plural fused rings, in which at least one ring atom is not carbon, i.e., a heteroatom. In the fused ring system, at least one heteroatom may be present in only one ring. For example, the heteroatom may be oxygen, sulfur, or nitrogen. Examples of the heteroaryl group include a furanyl group, a thienyl group, an imidazolyl group, a quinazolinyl group, a quinolinyl group, an isoquinolinyl group, a quinoxalinyl group, a pyridinyl group, a pyrrolyl group, an oxazolyl group, and an indolyl group.

The terms "aralkyl group" and "alkylaryl group" as used herein refer to an aryl group linked as a substituent via an alkylene group, such as a $C_7$-$C_{14}$ aralkyl group. Examples of the aralkyl group or alkylaryl group include a benzyl group, a 2-phenylethyl group, a 3-phenylpropyl group, and a naphthylalkyl group. In an embodiment, the alkylene group may be a lower alkylene group (i.e., a $C_1$-$C_4$ alkylene group).

The term "cycloalkenyl group" as used herein refers to a non-aromatic carbocyclic ring or ring system with at least one double bond. For example, the cycloalkenyl group may be a cyclohexenyl group.

The term "heterocyclic group" as used herein refers to a non-aromatic ring or ring system having at least one heteroatom in its ring backbone.

The term "halogen" as used herein refers to a stable element belonging to Group 17 of the periodic table, for example, fluorine, chlorine, bromine, or iodine. For example, the halogen may be fluorine and/or chlorine.

In the present specification, a substituent may be derived by substitution of at least one hydrogen atom in an unsubstituted mother group with another atom or a functional group. Unless stated otherwise, the term "substituted" indicates that the above-listed functional groups are substituted with at least one substituent selected from a $C_1$-$C_{40}$ alkyl group, a $C_2$-$C_{40}$ alkenyl group, a $C_3$-$C_{40}$ cycloalkyl group, a $C_3$-$C_{40}$ cycloalkenyl group, and a $C_7$-$C_4$n aryl group. The phrase "optionally substituted" as used herein indicates that the functional groups described above may be substituted with the aforementioned substituents or may be unsubstituted.

The amount of the bicyclic sulfate-based compound of Formula 1 as an additive in the organic electrolytic solution may range from about 0.4 wt % to about 5 wt % based on the total weight of the organic electrolytic solution. For example, the amount of the bicyclic sulfate-based compound of Formula 1 as an additive in the organic electrolytic solution may range from about 0.4 wt % to about 3 wt % based on the total weight of the organic electrolytic solution. For example, the amount of the bicyclic sulfate-based compound of Formula 1 in the organic electrolytic solution may range from about 0.6 wt % to about 3 wt % based on the total weight of the organic electrolytic solution. For example, the amount of the bicyclic sulfate-based compound of Formula 1 in the organic electrolytic solution may be from about 0.7 wt % to about 3 wt % based on the total weight of the organic electrolytic solution. For example, the amount of the bicyclic sulfate-based compound of Formula 1 in the organic electrolytic solution may be from about 0.4 wt % to about 2.5 wt % based on the total weight of the organic electrolytic solution. For example, the amount of the bicyclic sulfate-based compound of Formula 1 in the organic electrolytic solution may be from about 0.4 wt % to about 2 wt % based on the total weight of the organic electrolytic solution. For example, the amount of the bicyclic sulfate-based compound of Formula 1 in the organic electrolytic solution may be from about 0.4 wt % to about 1.5 wt % based on the total weight of the organic electrolytic solution. When the amount of the bicyclic sulfate-based compound of Formula 1 is within the ranges described above, further enhanced battery characteristics may be obtained.

The first lithium salt included in the organic electrolytic solution may include at least one selected from $LiPF_6$, $LiBF_4$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlCl_4$, $LiN(C_xF_{2x+1}SO_2)(C_yF_{2y+1}SO_2)$ where $2 \le x \le 20$ and $2 \le y \le 20$, LiCl, and LiI.

The concentration of the first lithium salt in the organic electrolytic solution may be, for example, from about 0.01 M to about 2.0 M. The concentration of the first lithium salt in the organic electrolytic solution may be appropriately adjusted as desired. When the concentration of the first lithium salt is within the above range, a battery with further enhanced characteristics may be obtained.

The organic solvent included in the organic electrolytic solution may be a low-boiling point solvent. The term "low-boiling point solvent" refers to a solvent having a boiling point of 200° C. or less at 1 atmosphere at 25° C.

For example, the organic solvent may include at least one selected from a dialkyl carbonate, a cyclic carbonate, a linear or cyclic ester, a linear or cyclic amide, an alicyclic nitrile, a linear or cyclic ether, and derivatives thereof.

For example, the organic solvent may include at least one selected from dimethyl carbonate (DMC), ethyl methyl carbonate (EMC), methyl propyl carbonate, ethyl propyl carbonate, diethyl carbonate (DEC), dipropyl carbonate, propylene carbonate (PC), ethylene carbonate (EC), butylene carbonate, ethyl propionate, ethyl butyrate, acetonitrile, succinonitrile (SN), dimethyl sulfoxide, dimethylformamide, dimethylacetamide, γ-valerolactone, γ-butyrolactone, and tetrahydrofuran. For example, the organic solvent may be a suitable solvent having a low-boiling point available in the art.

The organic electrolytic solution may further include other additives in addition to the bicyclic sulfate-based compound. Due to the further inclusion of other additives, a lithium battery with further enhanced performance may be obtained.

The additives further included in the organic electrolytic solution may include a cyclic carbonate compound, a second lithium salt, or the like.

For example, the organic electrolytic solution may further include a cyclic carbonate compound as an additive. The cyclic carbonate compound used as an additive may be selected from vinylene carbonate (VC), VC substituted with a halogen, a cyano (CN) group, or a nitro group ($NO_2$), vinyl ethylene carbonate (VEC), VEC substituted with a halogen, CN, or $NO_2$, fluoroethylene carbonate (FEC), or FEC substituted with a halogen, CN, or $NO_2$. When the organic electrolytic solution further includes a cyclic carbonate compound as an additive, a lithium battery including the organic electrolytic solution may have further enhanced charge and discharge characteristics.

The amount of the cyclic carbonate compound in the organic electrolytic solution may be, for example, from about 0.01 wt % to about 5 wt % based on the total weight of the organic electrolytic solution. The amount of the cyclic carbonate compound may be appropriately adjusted as desired. For example, the amount of the cyclic carbonate compound in the organic electrolytic solution may be from about 0.1 wt % to about 5 wt % based on the total weight of the organic electrolytic solution. For example, the amount of the cyclic carbonate compound in the organic electrolytic solution may be from about 0.1 wt % to about 4 wt % based on the total weight of the organic electrolytic solution. For example, the amount of the cyclic carbonate compound in the organic electrolytic solution may be from about 0.1 wt % to about 3 wt % based on the total weight of the organic electrolytic solution. For example, the amount of the cyclic carbonate compound in the organic electrolytic solution may be from about 0.1 wt % to about 2 wt % based on the total weight of the organic electrolytic solution. For example, the amount of the cyclic carbonate compound in the organic electrolytic solution may be from about 0.2 wt % to about 2 wt % based on the total weight of the organic electrolytic solution. For example, the amount of the cyclic carbonate compound in the organic electrolytic solution may be from about 0.2 wt % to about 1.5 wt % based on the total weight of the organic electrolytic solution. When the amount of the cyclic carbonate compound is within the above ranges, a battery with further enhanced characteristics may be obtained.

For example, the organic electrolytic solution may further include a second lithium salt as an additive. The second lithium salt is distinguished from (i.e., different from) the first lithium salt. An anion of the second lithium salt may be oxalate, $PO_2F_2$—, $N(SO_2F)_2$—, or the like. For example, the second lithium salt may be a compound represented by one of Formulae 18 to 25 below:

<Formula 18>

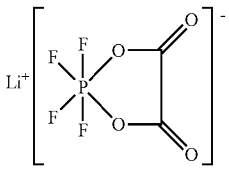

<Formula 19>

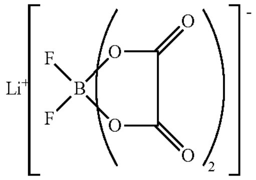

<Formula 20>

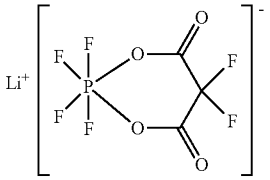

<Formula 21>

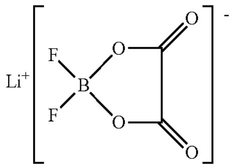

<Formula 22>

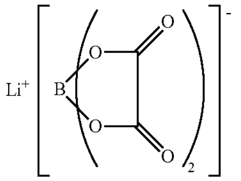

-continued

<Formula 23>

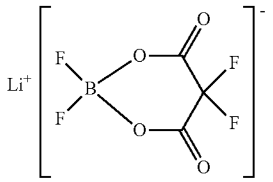

<Formula 24>

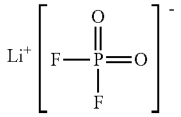

<Formula 25>

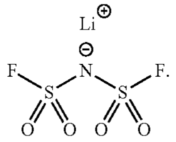

The amount of the second lithium salt in the organic electrolytic solution may be from about 0.1 wt % to about 5 wt % based on the total weight of the organic electrolytic solution. The amount of the second lithium salt may be appropriately adjusted if desired. For example, the amount of the second lithium salt in the organic electrolytic solution may be from about 0.1 wt % to about 4.5 wt % based on the total weight of the organic electrolytic solution. For example, the amount of the second lithium salt in the organic electrolytic solution may be from about 0.1 wt % to about 4 wt % based on the total weight of the organic electrolytic solution. For example, the amount of the second lithium salt in the organic electrolytic solution may be from about 0.1 wt % to about 3 wt % based on the total weight of the organic electrolytic solution. For example, the amount of the second lithium salt in the organic electrolytic solution may be from about 0.1 wt % to about 2 wt % based on the total weight of the organic electrolytic solution. For example, the amount of the second lithium salt in the organic electrolytic solution may be from about 0.2 wt % to about 2 wt % based on the total weight of the organic electrolytic solution. For example, the amount of the second lithium salt in the organic electrolytic solution may be from about 0.2 wt % to about 1.5 wt % based on the total weight of the organic electrolytic solution. When the amount of the second lithium salt is within the above ranges, a battery with further enhanced characteristics may be obtained.

The organic electrolytic solution may be in a liquid or gel state. The organic electrolytic solution may be prepared by adding the first lithium salt and the additive described above to the aforementioned organic solvent.

The nickel-containing layered lithium transition metal oxide included in the cathode of the lithium battery may be represented by, for example, Formula 26 below:

$$Li_aNi_xCo_yM_zO_{2-b}A_b \quad \text{<Formula 26>}$$

wherein, in Formula 26, $1.0 \le a \le 1.2$, $0 \le b \le 0.2$, $0.6 \le x < 1$, $0 < y \le 0.2$, $0 < z \le 0.2$, and $x+y+z=1$; M is at least one selected from manganese (Mn), vanadium (V), magnesium (Mg), gallium (Ga), silicon (Si), tungsten (W), molybdenum (Mo), iron (Fe), chromium (Cr), copper (Cu), zinc (Zn), titanium (Ti), aluminum (Al), and boron (B); and A is fluorine (F), sulfur (S), chlorine (Cl), bromine (Br), or a combination thereof. For example, $0.7 \le x < 1$, $0 < y \le 0.15$, $0 < z \le 0.15$, and $x+y+z=1$. For example, $0.75 \le x < 1$, $0 < y \le 0.125$, $0 < z \le 0.125$, and $x+y+z=1$. For example, $0.8\leq x<1$, $0<y\leq 0.1$, $0<z\leq 0.1$, and $x+y+z=1$. For example, $0.85\leq x<1$, $0<y\leq 0.075$, $0<z\leq 0.075$, and $x+y+z=1$.

The nickel-containing layered lithium transition metal oxide included in the cathode of the lithium battery may be represented by, for example, Formula 27 or 28:

$LiNi_xCo_yMn_zO_2$ <Formula 27>

$LiNi_xCo_yAl_zO_2$ <Formula 28> wherein, in Formulae 27 and 28, $0.6\leq x\leq 0.95$, $0<y\leq 0.2$, $0<z\leq 0.1$, and $x+y+z=1$. For example, $0.7\leq x\leq 0.95$, $0<y\leq 0.15$, $0<z\leq 0.15$, and $x+y+z=1$. For example, $0.75\leq x\leq 0.95$, $0<y\leq 0.125$, $0<z\leq 0.125$, and $x+y+z=1$. For example, $0.8\leq x\leq 0.95$, $0<y\leq 0.1$, $0<z\leq 0.1$, and $x+y+z=1$. For example, $0.85\leq x\leq 0.95$, $0<y\leq 0.075$, $0<z\leq 0.075$, and $x+y+z=1$.

The cathode active material may include a first lithium transition metal oxide and a second lithium transition metal oxide.

The first lithium transition metal oxide may be a large-diameter lithium transition metal oxide having a larger particle diameter than the second lithium transition metal oxide. The second lithium transition metal oxide may be, for example, a small-diameter lithium transition metal oxide having a smaller particle size than the first lithium transition metal oxide. For example, the second lithium transition metal oxide having a smaller particle diameter than the first lithium transition metal oxide may be disposed in pores between first lithium transition metal oxide particles. By disposing second lithium transition metal oxide particles, which are small-diameter particles, in pores between the first lithium transition metal oxide particles, which are large-diameter particles, the ionic conductivity and electronic conductivity of the cathode including a cathode active material can be simultaneously enhanced. In addition, the energy density of the cathode including a cathode active material may be enhanced. As a result, the lithium battery including the cathode active material may exhibit enhanced energy density and enhanced cycle characteristics.

The first lithium transition metal oxide and the second lithium transition metal oxide may have, for example, a bimodal particle size distribution in the particle size distribution diagram. For example, the composite positive electrode active material may have a bimodal particle size distribution having two peaks in a particle size distribution obtained using a particle size analyzer (PSA) or the like. The bimodal particle size distribution may have a first peak corresponding to the first lithium transition metal oxide and a second peak corresponding to the second lithium transition metal oxide.

A particle diameter ratio of the first lithium transition metal oxide and the second lithium transition metal oxide may be, for example, from about 3:1 to about 40:1, from about 3:1 to about 30:1, from about 3:1 to about 20:1, from about 3:1 to about 10:1, or from about 3:1 to about 5:1. When the particle diameter ratio of the first lithium transition metal oxide and the second lithium transition metal oxide is within these ranges, the energy density and cycle characteristics of the lithium battery including the cathode active material may be further enhanced.

The particle diameter of the first lithium transition metal oxide may be, for example, from greater than about 8 μm to about 30 μm, from about 9 μm to about 25 μm, from about 9 μm to about 20 μm, from about 9 μm to about 15 μm, or from about 9 μm to about 12 μm. The particle diameter of the first lithium transition metal oxide may be, for example, a median particle diameter (D50). The particle diameter of the second lithium transition metal oxide may be, for example, from about 1 μm to less than about 8 m, from about 1 μm to about 7 μm, from about 1 μm to about 6 μm, from about 1 μm to about 5 μm, or from about 1 μm to about 4 μm. The particle diameter of the first lithium transition metal oxide may be, for example, a median particle diameter (D50). When the particle diameters of the first lithium transition metal oxide and the second lithium transition metal oxide are within these ranges, the energy density and/or cycle characteristics of the lithium battery including the cathode active material may be further enhanced. The particle diameters of the first lithium transition metal oxide and the second lithium transition metal oxide are measured using, for example, a measurement device using a laser diffraction method or a dynamic light scattering method. The particle diameter is measured using, for example, a laser scattering particle size distribution meter (e.g., Horiba LA-920). The particle diameter is for example the median particle diameter (D50) which means cumulative diameters corresponding to 50 volume % from the small particle side.

A weight ratio of the first lithium transition metal oxide to the second lithium transition metal oxide may be, for example, from about 78:22 to about 60:40, from about 75:25 to about 60:40, or from about 70:30 to about 60:40. When the weight ratio of the first lithium transition metal oxide to the second lithium transition metal oxide is within these ranges, the energy density and/or cycle characteristics of the lithium battery including the composite cathode active material may be further enhanced.

The first lithium transition metal oxide may include, for example, a secondary particle including a plurality of primary particles, and the secondary particle may have a structure in which a plurality of primary particles are radially arranged. For example, the primary particles may be plate particles. Major axes of plate primary particles may be radially arranged. Accordingly, the secondary particle of the first lithium transition metal oxide may have a structure in which a plurality of plate primary particles are radially arranged. The term "radial" as used herein means that the thickness direction of the primary particles is arranged perpendicular to the direction from the surface of the secondary particle to the center of the secondary particle. The term "plate particle" as used herein means a particle whose thickness is smaller than the major axis length of the particle, that is, the in-plane length. The major axis length of the plate particle means the maximum length with respect to the widest side of the plate particle. The plate primary particle means, for example, a primary particle structure in which the length in one axial direction (i.e., thickness direction) of the primary particle is smaller than the major axis length in the other direction of the primary particle, i.e., in the plane direction. The plate primary particles may have, for example, a polygonal nanoplate shape such as a hexagon, a circular nanodisc shape, or a rectangular parallelepiped shape. A ratio of the average thickness to the average length of the plate primary particles may be from about 1:2 to about 1:10 or from about 1:2 to about 1:5. The structure in which the plurality of plate primary particles are radially arranged is a structure in which the thickness direction of the plurality of plate primary particles is perpendicular to the direction from the surface of the secondary particle to the center of the secondary particle. The secondary particle of the first lithium transition metal oxide has, for example, a structure in which a plurality of plate primary particles are radially arranged, and thus, the surfaces of the secondary particles of the first lithium transition metal oxide, the lithium diffusion path between relatively increased grain boundaries around the surfaces, and a crystal plane through which lithium can be transferred to the outside, for example, a (001) plane may be exposed a lot. Accordingly, the lithium diffusion rate may be increased in the secondary particles of the first lithium transition metal oxide having such a structure. Consequently, the lithium battery including the secondary particles of the first lithium transition metal oxide may enhanced initial efficiency and increased discharge capacity.

Examples of the lithium battery include lithium secondary batteries such as a lithium ion battery, a lithium ion polymer battery, a lithium sulfur battery, or the like, and lithium primary batteries.

For example, in the lithium battery, the anode may include graphite. For example, the lithium battery may have a high voltage of about 3.80 V or higher. For example, the lithium battery may have a high voltage of about 4.0 V or higher. For example, the lithium battery may have a high voltage of about 4.35 V or higher.

For example, the lithium battery may be manufactured using the following method.

A cathode may be prepared by a suitable method. For example, a cathode active material composition, in which the above-described cathode active material, a conductive material, a binder, and a solvent are mixed, may be prepared. The cathode active material composition may be directly coated onto a metal current collector, thereby completing the manufacture of a cathode plate. In some implementations, the cathode active material composition may be cast onto a separate support, and a film separated from the support may be laminated onto a metal current collector, thereby completing the manufacture of a cathode plate.

For example, the cathode active material may be a compound represented by any one of Formulae: $Li_aA_{1-b}B'_bD_2$ where $0.90 \le a \le 1.8$ and $0 \le b \le 0.5$; $Li_aE_{1-b}B'_bO_{2-c}D_c$ where $0.90 \le a \le 1.8$, $0 \le b \le 0.5$, and $0 \le c \le 0.05$; $LiE_{2-b}B'_bO_{4-c}D_c$ where $0 \le b \le 0.5$ and $0 \le c \le 0.05$; $Li_aNi_{1-b-c}Co_bB'_cD_\alpha$ where $0.90 \le a \le 1.8$, $0 \le b \le 0.5$, $0 \le c \le 0.05$, and $0 < \alpha \le 2$; $Li_aNi_{1-b-c}Co_bB'_cO_{2-\alpha}F'_\alpha$ where $0.90 \le a \le 1.8$, $0 \le b \le 0.5$, $0 \le c \le 0.05$, and $0 < \alpha < 2$; $LiaNi_{1-b-c}Co_bB'_cO_{2-\alpha}F'_2$ where $0.90 \le a \le 1.8$, $0 \le b \le 0.5$, $0 \le c \le 0.05$, and $0 < \alpha < 2$; $Li_aNi_{1-b-c}Mn_bB'_cD_\alpha$ where $0.90 \le a \le 1.8$, $0 \le b \le 0.5$, $0 \le c \le 0.05$, and $0 < \alpha \le 2$; $Li_aNi_{1-b-c}Mn_bB'_cO_{2-\alpha}F'_\alpha$ where $0.90 \le a \le 1.8$, $0 \le b \le 5$, $0 \le c \le 0.05$, and $0 < \alpha < 2$; $Li_aNi_{1-b-c}Mn_bB'_cCO_{2-\alpha}F'_2$ where $0.90 \le a \le 1.8$, $0 \le b \le 0.5$, $0 \le c \le 0.05$, and $0 < \alpha < 2$; $Li_aNi_bE_cG_dO_2$ where $0.90 \le a \le 1.8$, $0 \le b \le 0.9$, $0 \le c \le 0.5$, and $0.001 \le d \le 0.1$; $Li_aNi_bCo_cMn_dGeO_2$ where $0.90 \le a \le 1.8$, $0 \le b \le 0.9$, $0 \le c \le 0.5$, $0 \le d \le 0.5$, and $0.001 \le e \le 0.1$; $Li_aNiG_bO_2$ where $0.90 \le a \le 1.8$ and $0.001 \le b \le 0.1$; $Li_aCoG_bO_2$ wherein $0.90 \le a \le 1.8$ and $0.001 \le b \le 0.1$; $Li_aMnG_bO_2$ where $0.90 \le a \le 1.8$ and $0.001 \le b \le 0.1$; $Li_aMn_2G_bO_4$ where $0.90 \le a \le 1.8$ and $0.001 \le b \le 0.1$; $QO_2$; $QS_2$; $LiQS_2$; $V_2O_5$; $LiV_2O_5$; $LiI'O_2$; $LiNiVO_4$; $Li_{(3-f)}J_2(PO_4)_3$ where $0 \le f \le 2$; $Li_{(3-f)}Fe_2(PO_4)_3$ where $0 \le f \le 2$; and $LiFePO_4$.

In the formulae above, A may be selected from nickel (Ni), cobalt (Co), manganese (Mn), and combinations thereof; B' may be selected from aluminum (Al), Ni, Co, manganese (Mn), chromium (Cr), iron (Fe), magnesium (Mg), strontium (Sr), vanadium (V), a rare earth element, and combinations thereof, D may be selected from oxygen (O), fluorine (F), sulfur (S), phosphorus (P), and combinations thereof, E may be selected from Co, Mn, and combinations thereof; F' may be selected from F, S, P, and combinations thereof; G may be selected from Al, Cr, Mn, Fe, Mg, lanthanum (La), cerium (Ce), Sr, V, and combinations thereof; Q may be selected from titanium (Ti), molybdenum (Mo), Mn, and combinations thereof, I' may be selected from Cr, V, Fe, scandium (Sc), yttrium (Y), and combinations thereof, and J may be selected from V, Cr, Mn, Co, Ni, copper (Cu), and combinations thereof.

For example, the cathode active material may be $LiCoO_2$, $LiMn_xO_{2x}$ where x=1 or 2, $LiNi_{1-x}Mn_xO_{2x}$ where $0<x<1$, $LiNi_{1-x-y}Co_xMn_yO_2$ where $0<1-x-y<0.6$, $0 \le x \le 0.5$, and $0 \le y \le 0.5$, $LiFePO_4$, or the like.

In addition, the lithium-containing metal oxides described above used as a cathode active material may have a coating layer at their surfaces. In another embodiment, a mixture of a lithium-containing metal oxide and a lithium-containing metal oxide with a coating layer at a surface thereof may be used. The coating layer may include a coating element compound, such as an oxide of a coating element, a hydroxide of a coating element, an oxyhydroxide of a coating element, an oxycarbonate of a coating element, or a hydroxycarbonate of a coating element. The coating element compounds may be amorphous or crystalline. The coating element included in the coating layer may be selected from Mg, Al, Co, potassium (K), sodium (Na), calcium (Ca), silicon (Si), Ti, V, tin (Sn), germanium (Ge), gallium (Ga), boron (B), arsenic (As), zirconium (Zr), and mixtures thereof. A coating layer may be formed by using the coating elements in the aforementioned compounds by using a suitable method, (e.g., spray coating, dipping, or the like) that does not adversely affect physical properties of the cathode active material.

A suitable conductive material may be used. The conductive material may be, for example, carbon black, graphite particulates, or the like.

The binder may be a suitable binder used in the art. Examples of the binder include a vinylidene fluoride/hexafluoropropylene copolymer, polyvinylidene fluoride (PVDF), polyacrylonitrile, polymethyl methacrylate, polytetrafluoroethylene, mixtures thereof, and a styrene butadiene rubber-based polymer.

The solvent may be, for example, N-methylpyrrolidone, acetone, water, or the like.

The amounts of the cathode active material, the conductive material, the binder, and the solvent may be the same amounts as those used in a general lithium battery. At least one of the conductive material, the binder, and the solvent may be omitted according to the use and constitution of desired lithium batteries.

An anode may be prepared by a suitable fabrication method. For example, an anode active material composition may be prepared by mixing an anode active material, a conductive material, a binder, and a solvent. The anode active material composition may be directly coated onto a metal current collector and dried to obtain an anode plate. In some implementations, the anode active material composition may be cast onto a separate support and a film separated from the support may be laminated onto a metal current collector to complete the fabrication of an anode plate.

As the anode active material, a suitable anode active material for lithium batteries may be used. For example, the anode active material may include at least one selected from lithium metal, a metal alloyable with lithium, a transition metal oxide, a non-transition metal oxide, and a carbonaceous material.

For example, the metal alloyable with lithium may be Si, Sn, Al, Ge, lead (Pb), bismuth (Bi), antimony (Sb), a Si—Y' alloy (Y' is an alkali metal, an alkali earth metal, Group 13 and 14 elements, a transition metal, a rare earth element, or a combination thereof, and is not Si), a Sn—Y' alloy (Y' is an alkali metal, an alkali earth metal, Group 13 and 14 elements, a transition metal, a rare earth element, or a combination thereof, and is not Sn), or the like. The element Y' may be selected from Mg, Ca, Sr, barium (Ba), radium (Ra), Sc, Y, Ti, Zr, hafnium (Hf), rutherfordium (Rf), V, niobium (Nb), tantalum (Ta), dubnium (db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), zinc (Zn), cadmium (Cd), B, Al, Ga, Sn, indium (In), Ge, P, As, Sb, Bi, S, selenium (Se), tellurium (Te), polonium (Po), and combinations thereof.

For example, the transition metal oxide may be lithium titanium oxide, vanadium oxide, lithium vanadium oxide, or the like.

For example, the non-transition metal oxide may be $SnO_2$, SiOx where $0<x<2$, or the like.

For example, the carbonaceous material may be crystalline carbon, amorphous carbon, or a mixture thereof. Examples of the crystalline carbon include natural graphite and artificial graphite, each of which has an irregular form or is in the form of a plate, a flake, a sphere, or a fiber. Examples of the amorphous carbon include soft carbon (low-temperature calcined carbon), hard carbon, mesophase pitch carbonized product, and calcined coke.

In the anode active material composition, a conductive material and a binder that are the same as those used in the cathode active material composition may be used.

The amounts of the anode active material, the conductive material, the binder, and the solvent may be the same amounts as those used in a general lithium battery. At least one of the conductive material, the binder, and the solvent may be omitted according to the use and constitution of desired lithium batteries.

A suitable separator to be disposed between the cathode and the anode may be prepared. As the separator, a separator having low resistance to the transfer of ions in an electrolyte and having a high electrolyte-retaining ability may be used. Examples of the separator may include glass fiber, polyester, Teflon, polyethylene, polypropylene, polytetrafluoroethylene (PTFE), and combinations thereof, each of which may be a non-woven or woven fabric. For example, a windable separator formed of polyethylene, polypropylene, or the like may be used in lithium ion batteries, and a separator having a high organic electrolytic solution-retaining ability may be used in lithium ion polymer batteries. For example, the separator may be manufactured according to the following method.

A polymer resin, a filler, and a solvent may be mixed together to prepare a separator composition. Then, the separator composition may be directly coated onto an electrode and dried to form a separator. In an implementation, the separator composition may be cast onto a support and dried, and then a separator film separated from the support may be laminated onto an upper portion of an electrode, thereby completing the manufacture of a separator.

Suitable materials used in binders of electrode plates may in the manufacture of the separator. For example, the polymer resin may be a vinylidene fluoride/hexafluoropropylene copolymer, PVDF, polyacrylonitrile, polymethyl methacrylate, a mixture thereof, or the like.

The organic electrolytic solution as described above may be prepared.

Figure 7:
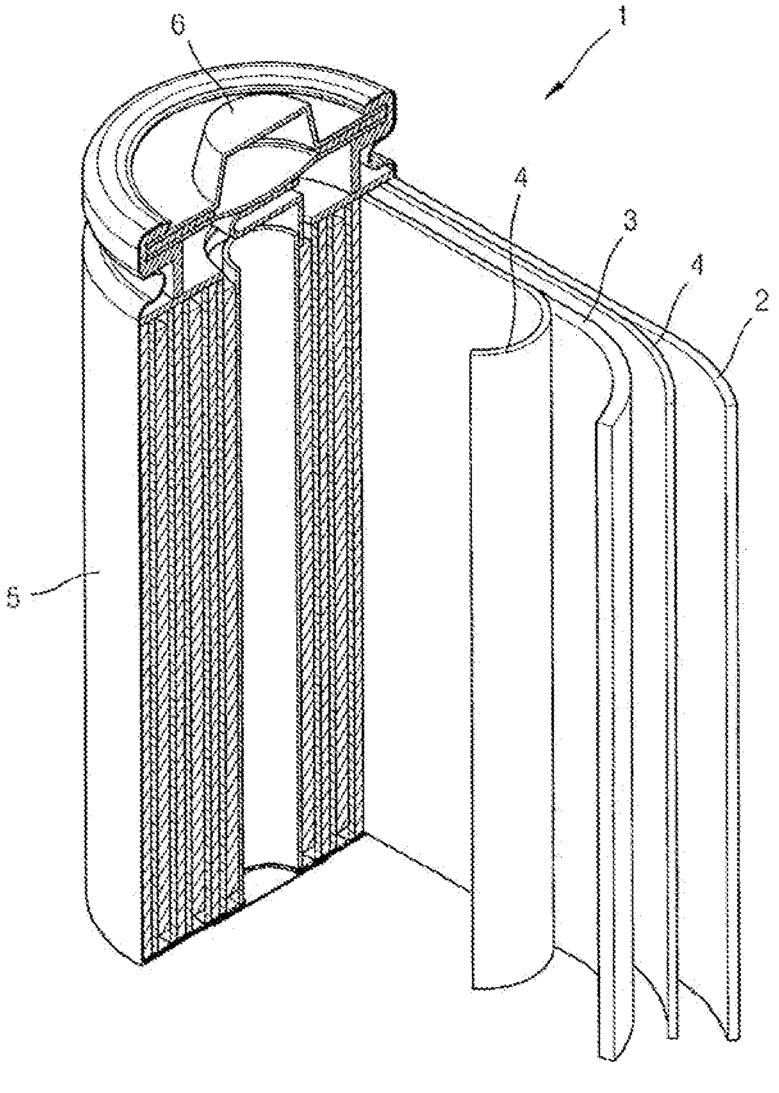
FIG. 7 illustrates a view of a lithium battery according to an embodiment.

As illustrated in FIG. 7, a lithium battery 1 may include a cathode 3, an anode 2, and a separator 4. The cathode 3, the anode 2, and the separator 4 may be wound or folded and then accommodated in a battery case 5. Subsequently, the organic electrolytic solution may be injected into the battery case 5, and the battery case 5 may be sealed with a cap assembly 6, thereby completing the manufacture of the lithium battery 1. The battery case 5 may have a cylindrical, rectangular or thin film shape.

In some implementations, the separator 4 may be disposed between the cathode 3 and the anode 2 to form a battery assembly, a plurality of battery assemblies may be stacked in a bi-cell structure and impregnated with the organic electrolytic solution, and the resultant may be put into a pouch and hermetically sealed, thereby completing the manufacture of a lithium battery.

The battery assemblies may be stacked to form a battery pack, and such a battery pack may be used in devices requiring high capacity and high-power output. For example, the battery pack may be used in notebook computers, smart phones, electric vehicles, or the like.

The lithium battery may have excellent lifespan characteristics and high rate characteristics, and thus, may be used in electric vehicles (EVs). For example, the lithium battery may be used in hybrid vehicles such as a plug-in hybrid electric vehicle (PHEV) or the like. The lithium battery may also be used in fields requiring the storage of a large amount of power. For example, the lithium battery may be used in electric bikes, motor-driven tools, or the like.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Additive

Preparation Example 1: Synthesis of Compound of Formula 3

The compound of Formula 3 may be prepared according to Reaction Scheme 1 below:

<Reaction Scheme 1>

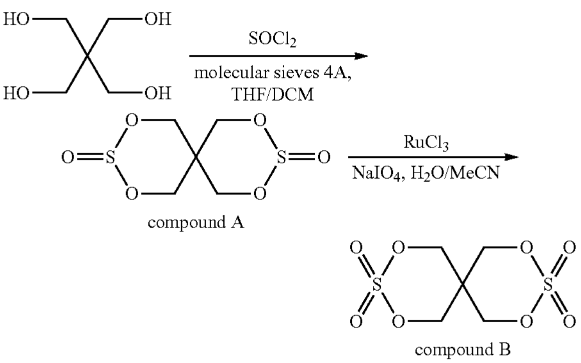

compound A compound B

Synthesis of Compound A 68.0 g (0.499 mol) of pentaerythritol and 100 g of molecular sieve (Type 4A) were added to a mixed solvent of tetrahydrofuran (THF) and dichloromethane (DCM, $CH_2Cl_2$) in a volume ratio of 1:1 and the resulting solution was refluxed for 20 minutes. Subsequently, 110 ml (2.8 equiv., 1.40 mol) of thionyl chloride ($SOCl_2$) was added to the resultant and the resultant solution was refluxed for 8 hours until the pentaerythritol was completely consumed by reaction, to obtain a light yellow solution. The obtained light yellow solution was filtered and concentrated to obtain a residue including a light yellow solid. Thereafter, 1 L of a saturated sodium hydrogen carbonate ($NaHCO_3$) solution was directly added to the residue at a rate at which effervescence was minimized, to obtain a suspension. The suspension was vigorously stirred for 20 minutes. Thereafter, the suspension was filtered and the obtained solid was added to 1 L of purified water to prepare a mixture. Then, the mixture was vigorously stirred for 20 minutes, subjected to suction filtration, and dried in air to obtain 104.61 g (0.458 mol) of Compound A (yield: 92%).

$^1$H-NMR and $^{13}$C-NMR data of Compound A were same as those in documents.

Synthesis of Compound B

As shown in Reaction Scheme 1 above, Compound B represented by Formula 6 below was synthesized from Compound A according to a method disclosed in Canadian Journal of Chemistry, 79, 2001, page 1042.

The synthesized compound was recrystallized in a mixed solvent of 1,2-dichloroethane and acetonitrile in a volume ratio of 2:1, which was then used in the preparation of an electrolytic solution.

Formula 6

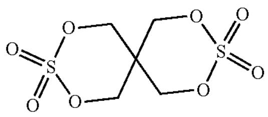

Preparation of Organic Electrolytic Solution

Example 1: SEI-1316 1.0 wt %

0.90 M $LiPF_6$ as a lithium salt and 1 wt % of the compound of Formula 6 were added to a mixed solvent of ethylene carbonate (EC), ethyl methyl carbonate (EMC), and diethyl carbonate (DEC) in a volume ratio of 3:5:2 to prepare an organic electrolytic solution.

<Formula 6>

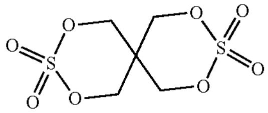

Example 2: SEI-1316 1.0 wt %+VC 0.5 wt %

An organic electrolytic solution was prepared in the same manner as in Example 1, except that 1 wt % of the compound of Formula 6 and 0.5 wt % of vinylene carbonate (VC) were used as additives.

Example 3: SEI-1316 0.5 wt %

An organic electrolytic solution was prepared in the same manner as in Example 1, except that the amount of the compound of Formula 6 used as an additive was changed to 0.5 wt %.

Example 4: SEI-1316 0.2 wt %

An organic electrolytic solution was prepared in the same manner as in Example 1, except that the amount of the compound of Formula 6 used as an additive was changed to 0.2 wt %.

Example 5: SEI-1316 0.3 wt %

An organic electrolytic solution was prepared in the same manner as in Example 1, except that the amount of the compound of Formula 6 used as an additive was changed to 0.3 wt %.

Example 6: SEI-1316 0.7 wt %

An organic electrolytic solution was prepared in the same manner as in Example 1, except that the amount of the compound of Formula 6 used as an additive was changed to 0.7 wt %.

Example 7: SEI-1316 1.5 wt %

An organic electrolytic solution was prepared in the same manner as in Example 1, except that the amount of the compound of Formula 6 used as an additive was changed to 1.5 wt %.

Example 8: SEI-1316 2 wt %

An organic electrolytic solution was prepared in the same manner as in Example 1, except that the amount of the compound of Formula 6 used as an additive was changed to 2 wt %.

Example 9: SEI-1316 3 wt %

An organic electrolytic solution was prepared in the same manner as in Example 1, except that the amount of the compound of Formula 6 used as an additive was changed to 3 wt %.

Example 9a: SEI-1316 4 wt %

An organic electrolytic solution was prepared in the same manner as in Example 1, except that the amount of the compound of Formula 6 used as an additive was changed to 4 wt %.

Example 10: SEI-1316 5 wt %

An organic electrolytic solution was prepared in the same manner as in Example 1, except that the amount of the compound of Formula 6 used as an additive was changed to 5 wt %.

Comparative Example 1: SEI-1316 0 wt %

An organic electrolytic solution was prepared in the same manner as in Example 1, except that the compound of Formula 6 used as an additive was not used.

Manufacture of Lithium Battery (Examples 1-1 to 3-1 and Comparative Example 1-1)

Example 1-1

Manufacture of Anode 98 wt % of artificial graphite (BSG-L manufactured by Tianjin BTR New Energy Technology Co., Ltd.), 1.0 wt % of styrene-butadiene rubber (SBR) (manufactured by Zeon) as a binder, and 1.0 wt % of carboxymethyl cellulose (CMC) (manufactured by NIPPON A&L) were mixed together, the mixture was added to distilled water, and the resulting solution was stirred using a mechanical stirrer for 60 minutes to prepare an anode active material slurry. The anode active material slurry was applied, using a doctor blade, onto a copper (Cu) current collector having a thickness of 10 μm to a thickness of about 60 μm, and the current collector was dried in a hot-air dryer at 100° C. for 0.5 hours, followed by further drying under conditions: in vacuum at 120° C. for 4 hours, and roll-pressed, thereby completing the manufacture of an anode plate.

Manufacture of Cathode 97.45 wt % of $LiNi_{1/3}Co_{1/3}Mn_{1/3}O_2$, 0.5 wt % of powder-type artificial graphite (SFG6 manufactured by Timcal) as a conductive material, 0.7 wt % of carbon black (Ketjen black manufactured by ECP), 0.25 wt % of modified acrylonitrile rubber (BM-720H manufactured by Zeon Corporation), 0.9 wt % of polyvinylidene fluoride (PVdF, S6020 manufactured by Solvay), and 0.2 wt % of PVdF (S5130 manufactured by Solvay) were mixed together, the mixture was added to N-methyl-2-pyrrolidone as a solvent, and the resulting solution was stirred using a mechanical stirrer for 30 minutes to prepare a cathode active material slurry. The cathode active material slurry was applied, using a doctor blade, onto an aluminum (Al) current collector having a thickness of 20 μm to a thickness of about 60 μm, and the current collector was dried in a hot-air dryer at 100° C. for 0.5 hours, followed by further drying under conditions: in vacuum at 120° C. for 4 hours, and roll-pressed, thereby completing the manufacture of a cathode plate.

A polyethylene separator having a thickness of 14 μm (manufactured by SK Innovation), a cathode side of which was coated with ceramic, and the organic electrolytic solution prepared according to Example 1 were used to complete the manufacture of a lithium battery.

Examples 2-1 and 3-1

Lithium batteries were manufactured in the same manner as in Example 1-1, except that the organic electrolytic solutions prepared according to Examples 2 and 3, respectively were used instead of the organic electrolytic solution of Example 1.

Comparative Example 1-1

A lithium battery was manufactured in the same manner as in Example 1-1, except that the organic electrolytic solution prepared according to Comparative Example 1 was used instead of the organic electrolytic solution of Example 1.

Evaluation Example 1: Evaluation of Charge and Discharge Characteristics at 4.25 V and Room Temperature (25° C.)

The lithium batteries manufactured according to Examples 1-1 to 3-1 and Comparative Example 1-1 were each charged at a constant current of 0.1 C rate at 25° C. until the voltage reached 4.25 V (vs. Li) and then, while maintaining a constant voltage of 4.25 V, the charging process was cut off at a current of 0.05 C rate. Subsequently, each lithium battery was discharged with a constant current of 0.1 C rate until the voltage reached 2.8 V (vs. Li) (formation operation, $1^{st}$ cycle).

Each lithium battery after the $1^{st}$ cycle of the formation operation was charged at a constant current of 0.2 C rate at 25° C. until the voltage reached 4.25 V (vs. Li) and then, while maintaining a constant voltage of 4.25 V, the charging process was cut off at a current of 0.05 C rate. Subsequently, each lithium battery was discharged at a constant current of 0.2 C rate until the voltage reached 2.8 V (vs. Li) (formation operation, $2^{nd}$ cycle).

Each lithium battery after the $2^{nd}$ cycle of the formation operation was charged at a constant current of 1.0 C rate at 25° C. until the voltage reached 4.25 V (vs. Li) and then, while maintaining a constant voltage of 4.25 V, the charging process was cut off at a current of 0.05 C rate. Subsequently, each lithium battery was discharged at a constant current of 1.0 C rate until the voltage reached 2.75 V (vs. Li), and this cycle of charging and discharging was repeated 380 times.

In all the cycles of charging and discharging, there was a rest period of 10 minutes at the end of each cycle of charging/discharging.

A part of the charging and discharging experiment results is shown in Table 1 below and FIGS. 1 and 2. A capacity retention ratio at the $380^{th}$ cycle is defined using Equation 1 below:

$$\text{Capacity retention ratio}=[\text{discharge capacity at } 380^{th} \text{ cycle}/\text{discharge capacity at } 1^{st} \text{ cycle}]\times 100 \quad \text{Equation 1}$$

TABLE 1

| | Discharge capacity at $380^{th}$ cycle [mAh/g] | Capacity retention ratio at $380^{th}$ cycle [%] |
|---|---|---|
| Example 1-1 | 202 | 75 |
| Example 2-1 | 228 | 82 |
| Comparative Example 1-1 | 173 | 63 |

Figure 2:
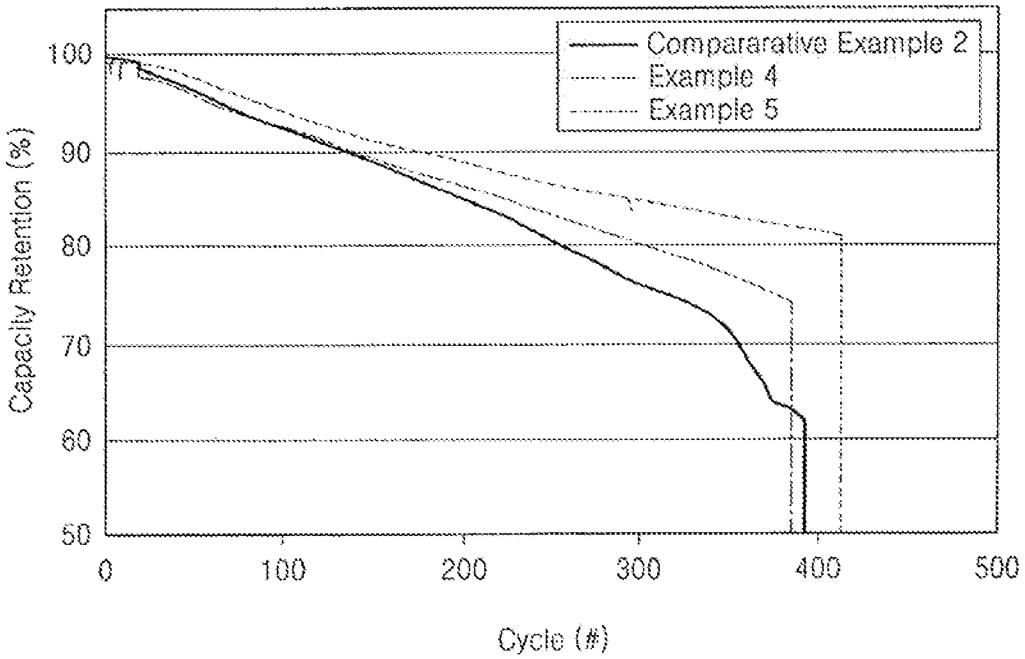
FIG. 2 illustrates a graph showing capacity retention ratios at room temperature of the lithium batteries of Examples 4 and 5 and Comparative Example 2.

As shown in Table 1 and FIGS. 1 and 2, the lithium batteries of Examples 1-1 and 2-1 including the additives according to embodiments of the present disclosure exhibited, at room temperature, significantly enhanced discharge capacities and lifespan characteristics, as compared to the lithium battery of Comparative Example 1-1 not including such an additive.

Evaluation Example 2: Evaluation of Charge and Discharge Characteristics at 4.25 V and High Temperature (45° C.)

Charge and discharge characteristics of the lithium batteries of Examples 1-1 to 3-1 and Comparative Example 1-1 were evaluated using the same method as that used in Evaluation Example 1, except that the charging and discharging temperature was changed to 45° C. Meanwhile, the number of charging and discharging cycles was changed to 200 cycles.

A part of the charging and discharging experiment results is shown in Table 2 below and FIGS. 3 and 4. A capacity retention ratio at the$_{200t}$h cycle is defined using Equation 2 below:

$$\text{Capacity retention ratio}=[\text{discharge capacity at } 200^{th} \text{ cycle}/\text{discharge capacity at } 1^{st} \text{ cycle}]\times 100 \quad \text{Equation 2}$$

TABLE 2

| | Discharge capacity at $200^{th}$ cycle [mAh/g] | Capacity retention ratio at $200^{th}$ cycle [%] |
|---|---|---|
| Example 1-1 | 249 | 83 |
| Example 2-1 | 255 | 84 |
| Comparative Example 1-1 | 235 | 79 |

Figure 3:
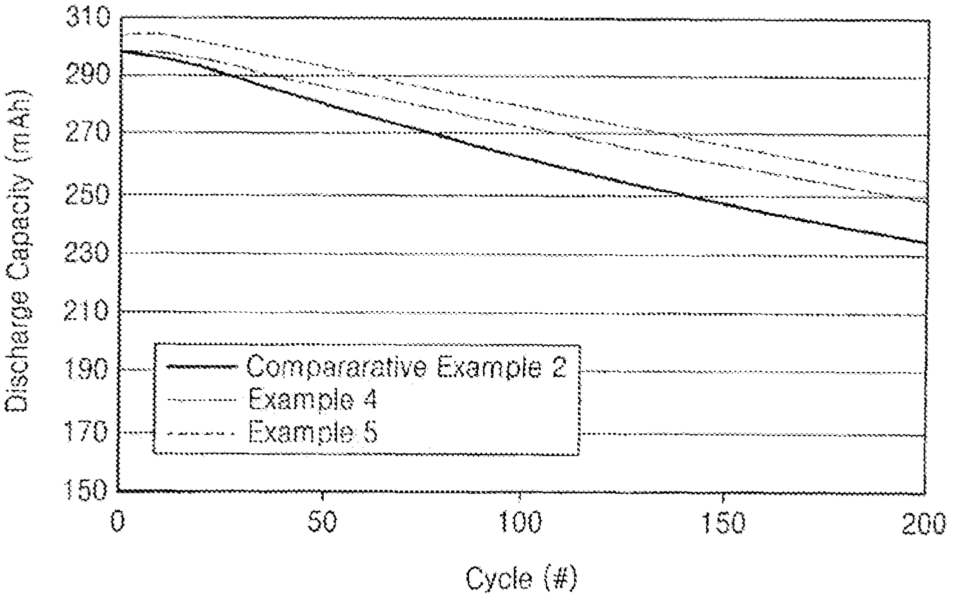
FIG. 3 illustrates a graph showing discharge capacities at a high temperature of the lithium batteries of Examples 4 and 5 and Comparative Example 2.
Figure 4:
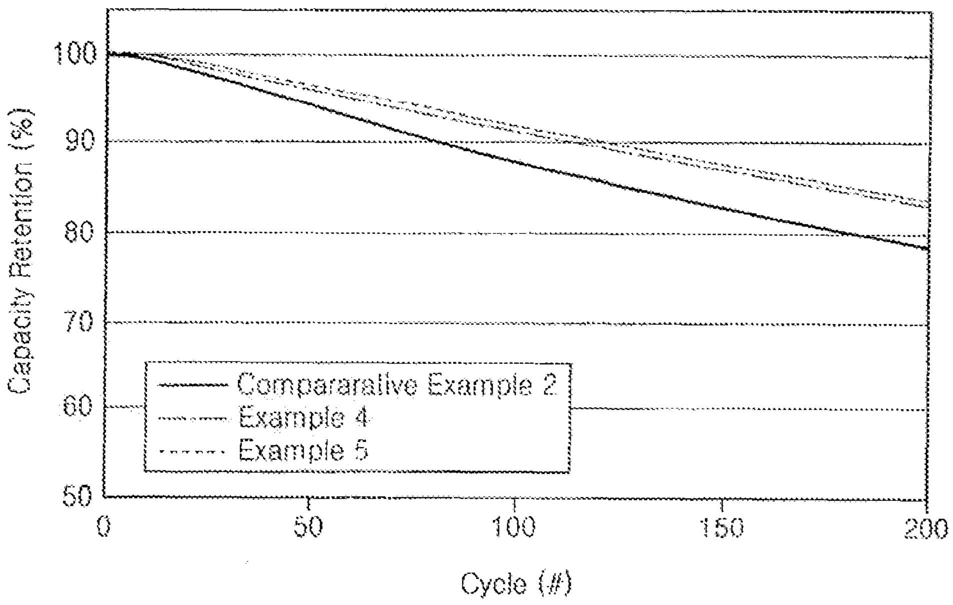
FIG. 4 illustrates a graph showing capacity retention ratios at a high temperature of the lithium batteries of Examples 4 and 5 and Comparative Example 2.

As shown in Table 2 and FIGS. 3 and 4, the lithium batteries of Examples 1-1 and 2-1 including the additives according to embodiments of the present disclosure exhibited, at a high temperature, significantly enhanced discharge capacities and lifespan characteristics, as compared to the lithium battery of Comparative Example 1-1 not including such an additive.

Evaluation Example 3: Evaluation of Charge and Discharge Characteristics at 4.30 V and Room Temperature (25° C.)

The lithium batteries of Example 1-1 and Comparative Example 1-1 were each charged at a constant current of 0.1 C rate at 25° C. until the voltage reached 4.30 V (vs. Li) and then, while maintaining a constant voltage of 4.30 V, the charging process was cut off at a current of 0.05 C rate. Subsequently, each lithium battery was discharged at a constant current of 0.1 C rate until the voltage reached 2.8 V (vs. Li) (formation operation, $1^{st}$ cycle).

Each lithium battery after the $1^{st}$ cycle of the formation operation was charged at a constant current of 0.2 C rate at 25° C. until the voltage reached 4.30 V (vs. Li) and then, while maintaining a constant voltage of 4.30 V, the charging process was cut off at a current of 0.05 C rate. Subsequently, each lithium battery was discharged at a constant current of 0.2 C rate until the voltage reached 2.8 V (vs. Li) (formation operation, $2^{nd}$ cycle).

Each lithium battery after the $2^{nd}$ cycle of the formation operation was charged at a constant current of 0.5 C rate at 25° C. until the voltage reached 4.30 V (vs. Li) and then, while maintaining a constant voltage of 4.30 V, the charging process was cut off at a current of 0.05 C rate. Subsequently, each lithium battery was discharged at a constant current of 1.0 C rate until the voltage reached 2.75 V (vs. Li), and this cycle of charging and discharging was repeated 250 times.

In all the cycles of charging and discharging, there was a rest period of 10 minutes at the end of each cycle of charging/discharging.

A part of the charging and discharging experiment results is shown in Table 3 below and FIG. 5. A capacity retention ratio at $250^{th}$ cycle is defined using Equation 3 below:

Capacity retention ratio=[discharge capacity at $250^{th}$ cycle/discharge capacity at 1st cycle]×100 — Equation 3

TABLE 3

| | Discharge capacity at $250^{th}$ cycle [mAh/g] | Capacity retention ratio at $250^{th}$ cycle [%] |
|---|---|---|
| Example 1-1 | 171 | 84 |
| Comparative Example 1-1 | 154 | 77 |

Figure 5:
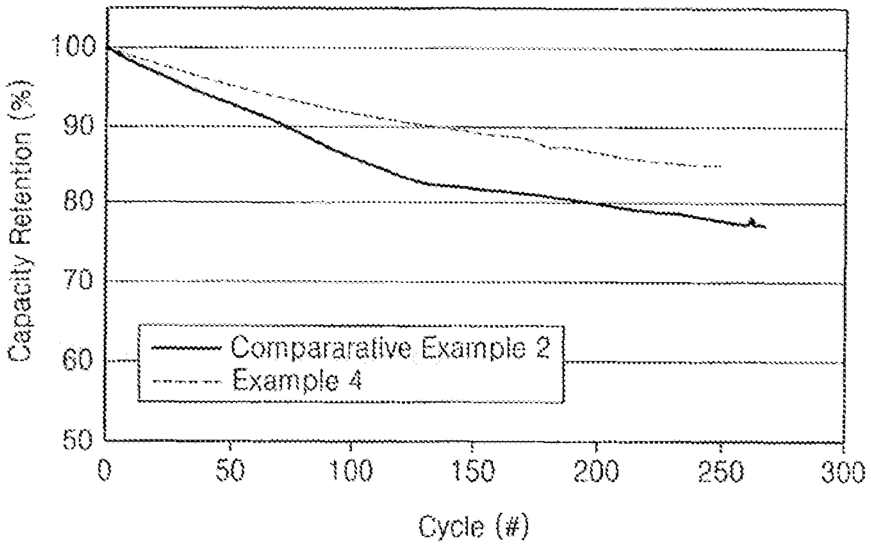
FIG. 5 illustrates a graph showing capacity retention ratios at room temperature of the lithium batteries of Example 4 and Comparative Example 2.

As shown in Table 3 and FIG. 5, the lithium battery of Example 1-1 including the additive according to an embodiment of the present disclosure exhibited, at room temperature, significantly enhanced discharge capacity and lifespan characteristics, as compared to the lithium battery of Comparative Example 1-1 not including such an additive.

Evaluation Example 4: Evaluation of Charge and Discharge Characteristics at 4.30 V and High Temperature (45° C.)

Charge and discharge characteristics of the lithium batteries of Example 1-1 and Comparative Example 1-1 were evaluated using the same method as that used in Evaluation Example 3, except that the charging and discharging temperature was changed to 45° C. Also, the number of charging and discharging cycles was changed to $200^{th}$ cycles.

A part of the charging and discharging experiment results is shown in Table 4 below and FIG. 6. A capacity retention ratio at the $200^{th}$ cycle is defined using Equation 4 below:

Capacity retention ratio=[discharge capacity at $200^{th}$ cycle/discharge capacity at $1^{st}$ cycle]×100 — Equation 4

TABLE 4

| | Discharge capacity at $200^{th}$ cycle [mAh/g] | Capacity retention ratio at $200^{th}$ cycle [%] |
|---|---|---|
| Example 1-1 | 189 | 90 |
| Comparative Example 1-1 | 174 | 84 |

Figure 6:
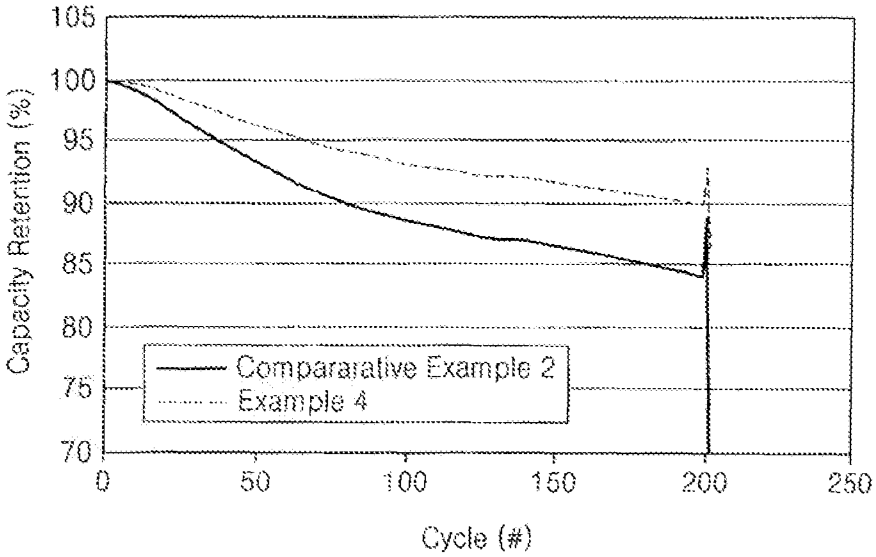
FIG. 6 illustrates a graph showing capacity retention ratios at a high temperature of the lithium batteries of Example 4 and Comparative Example 2.

As shown in Table 4 and FIG. 6, the lithium battery of Example 1-1 including the additive according to an embodiment of the present disclosure exhibited, at a high temperature, significantly enhanced discharge capacity and lifespan characteristics, as compared to the lithium battery of Comparative Example 1-1 not including such an additive.

Evaluation Example 5: High-Temperature (60° C.) Stability Evaluation

The lithium batteries of Examples 1-1 to 3-1 and Comparative Example 1-1 were subjected to the $1^{st}$ cycle of charging and discharging as follows. Each lithium battery was charged at a constant current of 0.5 C rate at 25° C. until the voltage reached 4.3 V and then, while maintaining a constant voltage of 4.3 V, each lithium battery was charged until the current reached 0.05 C and then discharged at a constant current of 0.5 C rate until the voltage reached 2.8 V.

Each lithium battery was subjected to the $2^{nd}$ cycle of charging and discharging as follows. Each lithium battery was charged at a constant current of 0.5 C rate until the voltage reached 4.3 V and then, while maintaining a constant voltage of 4.3 V, each lithium battery was charged until the current reached 0.05 C and then discharged at a constant current of 0.2 C rate until the voltage reached 2.8 V.

Each lithium battery was subjected to the $3^{rd}$ cycle of charging and discharging as follows. Each lithium battery was charged at a constant current of 0.5 C rate until the voltage reached 4.3 V and then, while maintaining a constant voltage of 4.3 V, each lithium battery was charged until the current reached 0.05 C and then discharged at a constant current of 0.2 C rate until the voltage reached 2.80 V. A discharge capacity at the $3^{rd}$ cycle was regarded as a standard capacity.

Each lithium battery was subjected to the $4^{th}$ cycle of charging and discharging as follows. Each lithium battery was charged at 0.5 C rate until the voltage reached 4.30 V and then, while maintaining a constant voltage of 4.30 V, each lithium battery was charged until the current reached 0.05 C, the charged battery was stored in an oven at 60° C. for 10 days and 30 days, and then the battery was taken out of the oven and then discharged at 0.1 C rate until the voltage reached 2.80 V.

A part of the charging and discharging evaluation results is shown in Table 5 below. A capacity retention ratio after the high-temperature storage is defined using Equation 5 below:

Capacity retention ratio after high-temperature storage [%]=[discharge capacity at high temperature at 4th cycle/standard capacity]×100 (herein, the standard capacity is a discharge capacity at 3rd cycle) Equation 5

TABLE 5

| | Capacity retention ratio after 10-day storage [%] | Capacity retention ratio after 30-day storage [%] |
|---|---|---|
| Example 3-1 | 91 | 87 |
| Comparative Example 1-1 | 90 | 86 |

As shown in Table 5, the lithium battery of Example 3-1 including the organic electrolytic solution according to an embodiment of the present disclosure exhibited significantly enhanced high-temperature stability, as compared to the lithium battery of Comparative Example 1-1 not including the organic electrolytic solution of the present invention.

Evaluation Example 6: Direct Current Resistance (DC-IR) Evaluation after High-Temperature (60° C.) Storage DC-IR of each of the lithium batteries of Examples 1-1 to 3-1 and Comparative Example 1-1, before being left sit in a 60° C. oven, after 10-day storage in an oven at 60° C., and after 30-day storage in an oven at 60° C., was measured at room temperature (25° C.) using the following method.

Each lithium battery was subjected to 1st cycle of charging and discharging as follows. Each lithium battery was charged at a current of 0.5 C until the voltage reached 50% SOC (state of charge), the charging process was cut off at 0.02 C, and then each lithium battery rested for 10 minutes. Subsequently, each lithium battery was subjected to the following processes: discharging at a constant current of 0.5 C for 30 seconds, followed by resting for 30 seconds, and charging at a constant current of 0.5 C for 30 seconds, followed by resting for 10 minutes; discharging at a constant current of 1.0 C for 30 minutes, followed by resting for 30 seconds, and charging at a constant current of 0.5 C for 1 minute, followed by resting for 10 minutes; discharging at a constant current of 2.0 C for 30 seconds, followed by resting for 30 seconds, and charging at a constant current of 0.5 C for 2 minutes, followed by resting for 10 minutes; discharging at a constant current of 3.0 C for 30 seconds, followed by resting for 30 seconds, and charging at a constant current of 0.5 C for 3 minutes, followed by resting for 10 minutes.

An average voltage drop value for 30 seconds at each C-rate is a direct current voltage value.

A part of direct current resistance increases calculated from measured initial direct current resistances and direct current resistances after high-temperature storage is shown in Table 6 below. A direct current resistance increase is represented by Equation 6 below:

Direct current resistance increase [%]=[direct current resistance after high-temperature storage/initial direct current resistance]×100 Equation 6

TABLE 6

| | Direct current resistance increase after 10-day storage [%] | Direct current resistance increase after 30-day storage [%] |
|---|---|---|
| Example 3-1 | 113 | 125 |
| Comparative Example 1-1 | 122 | 137 |

As shown in Table 6, the lithium battery of Example 3-1 including the organic electrolytic solution according to an embodiment of the present disclosure exhibited a decrease in direct current resistance increase after high-temperature storage, as compared to the lithium battery of Comparative Example 1-1 not including the organic electrolytic solution.

Manufacture of Lithium Battery (Examples A1 to A11, Reference Examples A1 to A5, and Comparative Examples A1 to A3)

Example A1: NCM, Ni60+SEI-1316 0.5 wt %

Manufacture of Anode 98 wt % of artificial graphite (BSG-L manufactured by Tianjin BTR New Energy Technology Co., Ltd.), 1.0 wt % of styrene-butadiene rubber (SBR) (manufactured by Zeon) as a binder, and 1.0 wt % of carboxymethyl cellulose (CMC) (manufactured by NIPPON A&L) were mixed together, the mixture was added to distilled water, and the resulting solution was stirred using a mechanical stirrer for 60 minutes to prepare an anode active material slurry. The anode active material slurry was applied, using a doctor blade, onto a Cu current collector having a thickness of 10 μm to a thickness of about 60 μm, and the current collector was dried in a hot-air dryer at 100° C. for 0.5 hours, followed by further drying in vacuum at 120° C. for 4 hours, and roll-pressed, thereby completing the manufacture of an anode plate.

Manufacture of Cathode 97.45 wt % of $Li_{1.02}Ni_{0.60}Co_{0.20}Mn_{0.20}O_2$, 0.5 wt % of powder-type artificial graphite (SFG6 manufactured by Timcal) as a conductive material, 0.7 wt % of carbon black (Ketjen black manufactured by ECP), 0.25 wt % of modified acrylonitrile rubber (BM-720H manufactured by Zeon Corporation), 0.9 wt % of polyvinylidene fluoride (PVdF) (S6020 manufactured by Solvay), and 0.2 wt % of PVdF (S5130 manufactured by Solvay) were mixed together, the mixture was added to N-methyl-2-pyrrolidone as a solvent, and the resulting solution was stirred using a mechanical stirrer for 30 minutes to prepare a cathode active material slurry. The cathode active material slurry was applied, using a doctor blade, onto an aluminum (Al) current collector having a thickness of 20 μm to a thickness of about 60 μm, and the current collector was dried in a hot-air dryer at 100° C. for 0.5 hours, followed by further drying in vacuum at 120° C. for 4 hours, and roll-pressed, thereby completing the manufacture of a cathode plate.

A polyethylene separator having a thickness of 14 μm, a cathode side of which was coated with ceramic, and the organic electrolytic solution prepared according to Example 3 were used as an electrolytic solution to complete the manufacture of a lithium battery.

Example A2: NCM, Ni60+SEI-1316 0.7 wt %

A lithium battery was manufactured in the same manner as in Example A1, except that the organic electrolytic solution prepared according to Example 6 was used as an electrolytic solution instead of the organic electrolytic solution of Example 3.

Example A3: NCM, Ni60+SEI-1316 1 wt %

A lithium battery was manufactured in the same manner as in Example A1, except that the organic electrolytic solution prepared according to Example 1 was used as an electrolytic solution instead of the organic electrolytic solution of Example 3.

Example A4: NCM, Ni60+SEI-1316 1.5 wt %

A lithium battery was manufactured in the same manner as in Example A1, except that the organic electrolytic solution prepared according to Example 7 was used as an electrolytic solution instead of the organic electrolytic solution of Example 3.

Example A5: NCM, Ni60+SEI-1316 3 wt %

A lithium battery was manufactured in the same manner as in Example A1, except that the organic electrolytic solution prepared according to Example 9 was used as an electrolytic solution instead of the organic electrolytic solution of Example 3.

Example A6: NCM, Ni88+SEI-1316 1 wt %

A lithium battery was manufactured in the same manner as in Example A1, except that $Li_{1.02}Ni_{0.88}Co_{0.08}Mn_{0.04}O_2$ was used as a cathode active material instead of $Li_{1.02}Ni_{0.60}Co_{0.20}Mn_{0.20}O_2$, and the organic electrolytic solution of Example 1 was used as an electrolytic solution.

Example A7: NCA, Ni88+SEI-1316 0.5 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$.

Example A8: NCA, Ni88+SEI-1316 0.7 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$, and the organic electrolytic solution of Example 6 was used as an electrolytic solution.

Example A9: NCA, Ni88+SEI-1316 1 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$, and the organic electrolytic solution of Example 1 was used as an electrolytic solution.

Example A10: NCA, Ni88+SEI-1316 3 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$, and the organic electrolytic solution prepared according to Example 9 was used as an electrolytic solution.

Example A11: NCA, Ni91+SEI-1316 1 wt %

A lithium battery was manufactured in the same manner as in Example A1, except that $Li_{1.02}Ni_{0.91}Co_{0.08}Al_{0.04}O_2$ was used as a cathode active material instead of $Li_{1.02}Ni_{0.60}Co_{0.20}Mn_{0.20}O_2$, and the organic electrolytic solution of Example 1 was used as an electrolytic solution.

Reference Example A1: Ni55+SEI-1316 1 wt %

A lithium battery was manufactured in the same manner as in Example A1, except that $Li_{1.02}Ni_{0.55}Co_{0.25}Mn_{0.20}O_2$ was used as a cathode active material instead of $Li_{1.02}Ni_{0.60}Co_{0.20}Mn_{0.20}O_2$, and the organic electrolytic solution of Example 1 was used as an electrolytic solution.

Reference Example A2: NCM, Ni60+SEI-1316 0.2 wt %

A lithium battery was manufactured in the same manner as in Example A1, except that the organic electrolytic solution prepared according to Example 4 was used as an electrolytic solution instead of the organic electrolytic solution of Example 3.

Reference Example A3: NCM, Ni60+SEI-1316 5 wt %

A lithium battery was manufactured in the same manner as in Example A1, except that the organic electrolytic solution prepared according to Example 10 was used as an electrolytic solution instead of the organic electrolytic solution of Example 3.

Reference Example A4: NCA, Ni88+SEI-1316 0.2 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$, and the organic electrolytic solution prepared according to Example 4 was used as an electrolytic solution instead of the organic electrolytic solution of Example 3.

Reference Example A5: NCA, Ni88+SEI-1316 5 wt %

A lithium battery was manufactured in the same manner as in Example A1, except that $Li_{1.02}Ni_{0.88}Co_{0.08}Al_{0.04}O_2$ was used as a cathode active material instead of $Li_{1.02}Ni_{0.60}Co_{0.20}Mn_{0.20}O_2$, and the organic electrolytic solution of Example 10 was used as an electrolytic solution instead of the organic electrolytic solution of Example 3.

Comparative Example A1: Ni60+SEI-1316 0 wt %

A lithium battery was manufactured in the same manner as in Example A1, except that the organic electrolytic solution prepared according to Comparative Example 1 was used as an electrolytic solution instead of the organic electrolytic solution of Example 3.

Comparative Example A2: LCO, Ni00+SEI-1316 1 wt %

A lithium battery was manufactured in the same manner as in Example A1, except that $LiCoO_2$ was used as a cathode active material instead of $Li_{1.02}Ni_{0.60}Co_{0.20}Mn_{0.20}O_2$, and the organic electrolytic solution of Example 1 was used as an electrolytic solution.

Comparative Example A3: NCM+LMO+SEI-1316 1 wt %

A lithium battery was manufactured in the same manner as in Example A1, except that a mixture of $LiNi_{1/3}Co_{1/3}Mn_{1/3}O_2$ and $LiMn_2O_4$ in a weight ratio of 1:1 was used as a cathode active material instead of $Li_{1.02}Ni_{0.85}Co_{0.10}Mn_{0.05}O_2$, and the organic electrolytic solution of Example 1 was used as an electrolytic solution.

Evaluation Example A1: Evaluation of Charge/Discharge Characteristics at 4.25 V and Room Temperature (25° C.)

Charge/discharge characteristics of the lithium batteries manufactured according to Examples A1 to A11, Reference Examples A1 to A5, and Comparative Examples A1 to A3 were evaluated using the same method as that used in Evaluation Example 1.

A part of the charging and discharging experiment results is shown in Table A1 below. A capacity retention ratio at the $380^{th}$ cycle is defined using Equation 1 below:

$$\text{Capacity retention ratio}=[\text{discharge capacity at } 380^{th} \text{ cycle}/\text{discharge capacity at } 1^{st} \text{ cycle}]\times 100 \quad \text{Equation 1}$$

TABLE A1

| | Capacity retention ratio at $380^{th}$ cycle [%] |
|---|---|
| Example A1 (NCM, Ni60 + SEI-1316 0.5 wt %) | 94 |
| Example A2 (NCM, Ni60 + SEI-1316 0.7 wt %) | 94 |
| Example A3 (NCM, Ni60 + SEI-1316 1 wt %) | 95 |
| Example A4 (NCM, Ni60 + SEI-1316 1.5 wt %) | 95 |
| Example A5 NCM, (Ni60 + SEI-1316 3 wt %) | 93 |
| Example A6 (NCM, Ni88 + SEI-1316 1 wt %) | 94 |
| Example A7 (NCA, Ni88 + SEI-1316 0.5 wt %) | 93 |
| Example A8 (NCA, Ni88 + SEI-1316 0.7 wt %) | 94 |
| Example A9 (NCA, Ni88 + SEI-1316 1 wt %) | 94 |
| Example A10 (NCA, Ni88 + SEI-1316 3 wt %) | 92 |
| Example A11 (NCA, Ni91 + SEI-1316 1 wt %) | 93 |
| Reference Example A1 (NCM, Ni55 + SEI-1316 1 wt %) | 90 |
| Reference Example A2 (NCM, Ni60 + SEI-1316 0.2 wt %) | 92 |
| Reference Example A3 (NCM, Ni60 + SEI-1316 5 wt %) wt %) | 93 |
| Reference Example A4 (NCA, Ni88 + SEI-1316 0.2 wt %) | 93 |
| Reference Example A5 (NCA, Ni88 + SEI-1316 5 wt %) | 91 |
| Comparative Example A1 (NCM, Ni60 + SEI-1316 0 wt %) | 85 |
| Comparative Example A2 (LCO, Ni00 + SEI-1316 1 wt %) | 83 |
| Comparative Example A3 (NCM + LMO + SEI-1316 1 wt %) | 85 |

As shown in Table A1, the lithium batteries of Examples A1 to A11 including the additives and the cathode active materials having high nickel content of the present disclosure exhibited significantly enhanced lifespan characteristics at room temperature, as compared to the lithium batteries of Reference Examples A1 and A2 and Comparative Example A1, including a cathode active material having low nickel content or not including an additive.

In addition, the lithium batteries of Examples A1 to A11 each including a certain amount of additive exhibited more enhanced lifespan characteristics at room temperature than those of the lithium batteries of Reference Examples A4 to A7 each including an additive in an amount outside the certain range.

Evaluation Example A2: Direct Current-Internal Resistance (DC-IR) Evaluation after High-Temperature (60° C.) Storage DC-IRs after high-temperature storage of the lithium batteries of Examples A1 to A11, Reference Examples A1 to A7, and Comparative Example A1 were measured using the same method as that used in Evaluation Example 6.

A part of DC-IR increases, which were obtained by calculation using the measured initial DC-IRs and the measured DC-IRs after high-temperature storage, is shown in Table A2 below. A DC-IR increase is represented by Equation 6 below:

$$\text{Direct current internal resistance increase [\%]}=[\text{direct current internal resistance after high-temperature storage}/\text{initial direct current internal resistance}]\times 100 \quad \text{Equation 6}$$

TABLE A2

| | Direct current internal resistance increase after 30-day storage [%] |
|---|---|
| Example A1 (NCM, Ni60 + SEI-1316 0.5 wt %) | 128.4 |
| Example A2 (NCM, Ni60 + SEI-1316 0.7 wt %) | 127.0 |
| Example A3 (NCM, Ni60 + SEI-1316 1 wt %) | 125.3 |
| Example A4 (NCM, Ni60 + SEI-1316 1.5 wt %) | 124.8 |
| Example A5 NCM, (Ni60 + SEI-1316 3 wt %) | 126.2 |
| Example A6 (NCM, Ni88 + SEI-1316 1 wt %) | 127.6 |
| Example A7 (NCA, Ni88 + SEI-1316 0.5 wt %) | 128.1 |
| Example A8 (NCA, Ni88 + SEI-1316 0.7 wt %) | 128.1 |
| Example A9 (NCA, Ni88 + SEI-1316 1 wt %) | 126.4 |
| Example A10 (NCA, Ni88 + SEI-1316 3 wt %) | 128.3 |
| Example A11 (NCA, Ni91 + SEI-1316 1 wt %) | 126.1 |
| Reference Example A1 (NCM, Ni55 + SEI-1316 1 wt %) | 137.1 |
| Reference Example A2 (NCM, Ni60 + SEI-1316 0.2 wt %) | 132.3 |
| Reference Example A3 (NCM, Ni60 + SEI-1316 5 wt %) | 130.0 |
| Reference Example A4 (NCA, Ni88 + SEI-1316 0.2 wt %) | 130.0 |
| Reference Example A5 (NCA, Ni88 + SEI-1316 5 wt %) | 132.7 |
| Comparative Example A1 (NCM, Ni60 + SEI-1316 0 wt %) | 135.2 |
| Comparative Example A2 (LCO, Ni00 + SEI-1316 1 wt %) | 141.3 |
| Comparative Example A3 (NCM + LMO + SEI-1316 1 wt %) | 139.5 |

As shown in Table A2, the lithium batteries of Examples A1 to A11 including the additives and the cathode active materials having high nickel content of the present disclosure exhibited a lower DC-IR increase than that of each of the lithium batteries of Comparative Examples A1 to A3, which included a cathode active material having low nickel content and did not include an additive.

In addition, the lithium batteries of Examples A1 to A11 each including a certain amount of additive exhibited a lower DC-IR increase than that of each of the lithium batteries of Reference Examples A1 to A5 including an additive in an amount outside the certain range.

Manufacture of Lithium Battery

Example J1: Large Diameter: Small Diameter (One Body)=70:30+SEI-1316 1.0 wt %

Manufacture of Anode 98 wt % of artificial graphite (BSG-L manufactured by Tianjin BTR New Energy Technology Co., Ltd.), 1.0 wt % of styrene-butadiene rubber (SBR) (manufactured by Zeon) as a binder, and 1.0 wt % of carboxymethyl cellulose (CMC) (manufactured by NIPPON A&L) were mixed together, the mixture was added to distilled water, and the resulting solution was stirred using a mechanical stirrer for 60 minutes to prepare an anode active material slurry. The anode active material slurry was applied, using a doctor blade, onto a copper (Cu) current collector having a thickness of 10 μm to a thickness of about 60 μm, and the current collector was dried in a hot-air dryer at 100° C. for 0.5 hours, followed by further drying under conditions: in vacuum at 120° C. for 4 hours, and roll-pressed, thereby completing the manufacture of an anode plate.

Manufacture of Cathode

A mixture of $LiNi_{0.91}Co_{0.08}Al_{0.04}O_2$ (hereinafter, referred to as large-diameter NCA91) as large-diameter particles having an average particle diameter of 10 μm, and $LiNi_{0.91}Co_{0.08}Al_{0.04}O_2$ (hereinafter, referred to as small-diameter NCA91) as small-diameter particles having an average particle diameter of 3 μm in a weight ratio of 70:30 was prepared.

The large-diameter NCA is a secondary particle as an agglomerate of a plurality of primary particles having an average particle diameter of less than 1 μm. The small-diameter NCA is a single crystal one-body particle consisting of a single primary particle.

The large-diameter NCA91 is a secondary particle having a structure in which a plurality of plate primary particles are radially arranged. The plurality of plate primary particles included in the large-diameter NCA91 had a structure in which major axes thereof are radially arranged.

A mixture of a cathode active material mixture, a carbon conductive agent (Denka Black), and polyvinylidene fluoride (PVdF) in a weight ratio of 96:2:2 was added to N-methyl-2-pyrrolidone as a solvent, and the resulting solution was stirred using a mechanical stirrer for 30 minutes to prepare a cathode active material slurry. The cathode active material slurry was applied, using a doctor blade, onto an aluminum (A1) current collector having a thickness of 20 μm to a thickness of about 60 μm, and the current collector was dried in a hot-air dryer at 100° C. for 0.5 hours, followed by further drying under conditions: in vacuum at 120° C. for 4 hours, and roll-pressed, thereby completing the manufacture of a cathode plate.

A polyethylene separator having a thickness of 14 μm, a cathode side of which was coated with ceramic, and the organic electrolytic solution prepared according to Example 1 as an electrolytic solution were used to complete the manufacture of a lithium battery.

Example J2: Large Diameter: Small Diameter (One Body)=70:30+SEI-1316 0.5 wt %

A lithium battery was manufactured in the same manner as in Example H1, except that the organic electrolytic solution prepared according to Example 3 was used as an electrolytic solution.

Example J3: Large Diameter: Small Diameter (One Body)=70:30+SEI-1316 2.0 wt %

A lithium battery was manufactured in the same manner as in Example H1, except that the organic electrolytic solution prepared according to Example 8 was used as an electrolytic solution.

Example J4: Large Diameter: Small Diameter (One Body)=70:30+SEI-1316 3.0 wt %

A lithium battery was manufactured in the same manner as in Example H1, except that the organic electrolytic solution prepared according to Example 9 was used as an electrolytic solution.

Example J5: Large Diameter: Small Diameter (One Body)=70:30+SEI-1316 5.0 wt %

A lithium battery was manufactured in the same manner as in Example J1, except that the organic electrolytic solution prepared according to Example 10 was used as an electrolytic solution.

Example J6: Large Diameter: Small Diameter (One Body)=60:40+SEI-1316 5.0 wt %

A lithium battery was manufactured in the same manner as in Example J1, except that a mixture of large-diameter NCA and small-diameter NCA in a weight ratio of 60:40 was used as a cathode active material.

Comparative Example J1: Large Diameter:Small Diameter (One Body)=70:30+SEI-1316 0 wt %

A lithium battery was manufactured in the same manner as in Example J1, except that the organic electrolytic solution of Comparative Example 1 was used as an electrolytic solution.

Comparative Example J2: Large Diameter:Small Diameter (One Body)=100:0+SEI-1316 0 wt %

A lithium battery was manufactured in the same manner as in Example J1, except that the organic electrolytic solution of Comparative Example 1 was used as an electrolytic solution, and as the cathode active material, only large-diameter NCA was used and small-diameter NCA was not used.

Comparative Example J3: Large Diameter:Small Diameter (One Body)=100:0+SEI-1316 1.0 wt %

A lithium battery was manufactured in the same manner as in Example J1, except that, as the cathode active material, large-diameter NCA was used alone and small-diameter NCA was not used.

Comparative Example J4: Large Diameter:Small Diameter (One Body)=90:10+SEI-1316 1.0 wt %

A lithium battery was manufactured in the same manner as in Example J1, except that a mixture of large-diameter NCA and small-diameter of NCA in a weight ratio of 90:10 was used as a cathode active material.

Comparative Example J5: Large Diameter:Small Diameter (One Body)=80:20+SEI-1316 1.0 wt %

A lithium battery was manufactured in the same manner as in Example J1, except that a mixture of large-diameter NCA and small-diameter of NCA in a weight ratio of 80:20 was used as a cathode active material.

Comparative Example J6: Large Diameter:Small Diameter (One Body)=50:50+SEI-1316 1.0 wt %

A lithium battery was manufactured in the same manner as in Example J1, except that a mixture of large-diameter NCA and small-diameter of NCA in a weight ratio of 50:50 was used as a cathode active material.

Comparative Example J7: Large Diameter:Small Diameter (Secondary Particle)=70:30+SEI-1316 1.0 wt %

A lithium battery was manufactured in the same manner as in Example J1, except that secondary particles as agglomerates of a plurality of primary particles were used as small-diameter NCA particles instead of a one-body particle (the primary particles having an average particle diameter of less than 1 μm, and the secondary particles having an average particle diameter of 3 μm).

Evaluation Example J1: Evaluation of Charge and Discharge Characteristics at 4.25 V and High Temperature (45° C.)

Charge and discharge characteristics of the lithium batteries of Examples J1 to J10, Reference Examples J1 to J4, and Comparative Examples J1 to J4 at high temperature were evaluated using the same method as that used in Evaluation Example 2. In this regard, the number of cycles of charging and discharging was changed to 300 cycles.

A part of the charging and discharging experiment results is shown in Table J1 below. A capacity retention ratio at the $300^{th}$ cycle is defined using Equation J1 below:

Capacity retention ratio=[discharge capacity at $300^{th}$ cycle/discharge capacity at $1^{st}$ cycle]×100 Equation J1

TABLE J1

| | Capacity retention ratio at $300^{th}$ cycle [%] |
|---|---|
| Example J1: Large diameter:small diameter (one body) = 70:30 + SEI-1316 1.0 wt % | 94 |
| Example J2: Large diameter:small diameter (one body) = 70:30 + SEI-1316 0.5 wt % | 94 |
| Example J3: Large diameter:small diameter (one body) = 70:30 + SEI-1316 2.0 wt % | 93 |
| Example J4: Large diameter:small diameter (one body) = 70:30 + SEI-1316 3.0 wt % | 93 |
| Example J5: Large diameter:small diameter (one body) = 70:30 + SEI-1316 5.0 wt % | 92 |
| Example J6: Large diameter:small diameter (one body) = 60:40 + SEI-1316 1.0 wt % | 93 |
| Comparative Example J1: Large diameter:small diameter (one body) = 70:30 + SEI-1316 0 wt % | 89 |
| Comparative Example J2: Large diameter:small diameter (one body) = 100:0 + SEI-1316 0 wt % | 88 |
| Comparative Example J3: Large diameter:small diameter (one body) = 100:0 + SEI-1316 1.0 wt % | 91 |
| Comparative Example J4: Large diameter:small diameter (one body) = 90:10 + SEI-1316 1.0 wt % | 91 |
| Comparative Example J5: Large diameter:small diameter (one body) = 80:20 + SEI-1316 1.0 wt % | 91 |
| Comparative Example J6: Large diameter:small diameter (one body) = 50:50 + SEI-1316 1.0 wt % | 91 |
| Comparative Example J7: Large diameter:small diameter (secondary particles) = 70:30 + SEI-1316 1.0 wt % | 90 |

As shown in Table J1, the lithium batteries of Examples J1 to J6 including the additives according to the present disclosure exhibited significantly enhanced lifespan characteristics at high temperature, as compared to the lithium batteries of Comparative Examples J1 and J2 not including an additive.

The lithium batteries of Examples J1 to J6 in which the amount of large-diameter particles was less than 80 wt % and greater than 50 wt % exhibited enhanced lifespan characteristics, as compared to the lithium batteries of Comparative Examples J3 to J6 including large-diameter particles in an amount outside this range.

The lithium batteries of Examples J1 to J6 including primary particles (one-body particles) as small-diameter particles exhibited enhanced lifespan characteristics at high temperature, as compared to the lithium battery of Comparative Example J7 including secondary particles as small-diameter particles.

Evaluation Example J2: Direct current-internal resistance (DC-IR) evaluation after evaluation of lifespan characteristics at high temperature DC-IRs of the lithium batteries manufactured according to Examples J1 to J10, Reference Examples J1 to J4, and Comparative Examples J1 to J4 and the lithium batteries thereof after the lifespan characteristics at high temperature were evaluated according to Evaluation Example J1 were measured using the following method.

In the $1^{st}$ cycle, each lithium battery was charged at a current of 0.5 C until the voltage reached 50% SOC (state of charge), followed by resting for 10 minutes, and was discharged at a constant current of 1.0 C for 30 minutes.

The current applied during discharging for 30 minutes and the voltage after discharging were measured, and DC-IR was calculated therefrom.

Initial direct current resistances of the lithium batteries manufactured according to Examples J1 to J10, Reference Examples J1 to J4, and Comparative Examples J1 to J4 were measured.

DC-IRs of the lithium batteries after the lifespan characteristics at high temperature were evaluated according to Evaluation Example J1 were measured.

A part of direct current resistance increases calculated from the measured initial direct current resistances and the direct current resistances after the evaluation of lifespan characteristics at high temperature is shown in Table J2 below. A direct current resistance increase is represented by Equation J2 below:

Direct current resistance increase [%]=[direct current resistance after evaluation of lifespan characteristics at high temperature/initial direct current resistance]×100 Equation J2

TABLE J2

| | Capacity retention ratio at $300^{th}$ cycle [%] |
|---|---|
| Example J1: Large diameter:small diameter (one body) = 70:30 + SEI-1316 1.0 wt % | 34.8 |
| Example J2: Large diameter:small diameter (one body) = 70:30 + SEI-1316 0.5 wt % | 37.3 |
| Example J3: Large diameter:small diameter (one body) = 70:30 + SEI-1316 2.0 wt % | 35.2 |
| Example J4: Large diameter:small diameter (one body) = 70:30 + SEI-1316 3.0 wt % | 37.5 |
| Example J6: Large diameter:small diameter (one body) = 60:40 + SEI-1316 1.0 wt % | 37.3 |
| Comparative Example J1: Large diameter:small diameter (one body) = 70:30 + SEI-1316 0 wt % | 51.6 |
| Comparative Example J2: Large diameter:small diameter (one body) = 100:0 + SEI-1316 0 wt % | 64.9 |
| Comparative Example J3: Large diameter:small diameter (one body) = 100:0 + SEI-1316 1.0 wt % | 47.8 |
| Comparative Example J4: Large diameter:small diameter (one body) = 90:10 + SEI-1316 1.0 wt % | 42.9 |
| Comparative Example J5: Large diameter:small diameter (one body) = 80:20 + SEI-1316 1.0 wt % | 39.6 |
| Comparative Example J6: Large diameter:small diameter (one body) = 50:50 + SEI-1316 1.0 wt % | 38.0 |
| Comparative Example J7: Large diameter:small diameter (secondary narticles) = 70:30 + SEI-1316 1.0 wt % | 49.3 |

As shown in Table J2, the lithium batteries of Examples J1 to J6 including the additives of the present disclosure exhibited a lower DC-IR increase than that of each of the lithium batteries of Comparative Examples J1 and J2, which did not include an additive.

Although not shown in Table J2, Example J5 exhibited a direct current resistance increase similar to that of Example J4.

The lithium batteries of Examples J1 to J6 in which the amount of large-diameter particles is less than 80 wt % and greater than 50 wt % exhibited a lower direct current resistance increase than that of each of the lithium batteries of Comparative Examples J3 to J6 including large-diameter particles in an amount outside this range.

The lithium batteries of Examples J1 to J6 including primary particles (one-body particles) as small-diameter particles exhibited a lower direct current resistance increase than that of the lithium battery of Comparative Example J7 including secondary particles as small-diameter particles.

As is apparent from the foregoing description, a lithium battery including a cathode including a large-diameter lithium transition metal oxide and a small-diameter lithium transition metal oxide, in which the small-diameter lithium transition metal oxide has a one-body particle form, and an organic electrolytic solution including a novel bicyclic sulfate-based additive may exhibit enhanced high-temperature characteristics and lifespan characteristics.

By way of summation and review, when lithium batteries operate at high operating voltages, aqueous electrolytic solutions highly reactive to lithium may not be suitable for use in such lithium batteries. Lithium batteries generally use organic electrolytic solutions. An organic electrolytic solution is prepared by dissolving a lithium salt in an organic solvent. An organic solvent with stability at high voltages, high ionic conductivity, high dielectric constant, and low viscosity may be used.

When a lithium battery uses a general organic electrolytic solution including a carbonate-based polar non-aqueous solvent, an irreversible reaction, in which charges are excessively used due to a side reaction between the anode/cathode and the organic electrolytic solution, may occur during initial charging. As a result of such an irreversible reaction, a passivation layer, such as a solid electrolyte interface (SEI) layer, may be formed at a surface of an anode. In addition, a protection layer is formed at a surface of a cathode.

In this regard, the SEI layer and/or the protection layer, formed using an existing organic electrolytic solution, may be easily degraded. For example, such an SEI layer and/or protection layer may exhibit decreased stability at a high temperature.

Therefore, an organic electrolytic solution capable of forming an SEI layer and/or a protection layer having improved high-temperature stability is desirable.

Embodiments provide a lithium battery including a cathode including a lithium transition metal oxide having high nickel content and an organic electrolytic solution including a novel bicyclic sulfate-based additive. The lithium battery according to embodiments exhibits enhanced high-temperature characteristics and lifespan characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A lithium battery, comprising:

a cathode including a cathode active material;

an anode including an anode active material; and an organic electrolytic solution between the cathode and the anode, wherein:

the cathode active material includes a first lithium transition metal oxide and a second lithium transition metal oxide, the first lithium transition metal oxide and the second lithium transition metal oxide have different particle diameters, the second lithium transition metal oxide includes primary particles having a particle diameter of about 1 μm or more, an amount of the bicyclic sulfate-based compound is from about 0.1 wt % to about 5 wt % based on a total weight of the organic electrolytic solution, a particle diameter ratio of the first lithium transition metal oxide to the second lithium transition metal oxide is from about 3:1 to about 40:1, the first lithium transition metal oxide has a particle diameter of greater than about 8 μm to about 30 μm, the second lithium transition metal oxide has a particle diameter of about 1 μm to less than about 8 μm, a weight ratio of the first lithium transition metal oxide to the second lithium transition metal oxide is from about 78:22 to about 60:40, and the organic electrolytic solution includes a first lithium salt, an organic solvent, and a bicyclic sulfate-based compound represented by Formula 1 below:

<Formula 1>

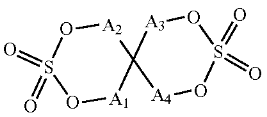

wherein, in Formula 1, each of $A_1$, $A_2$, $A_3$, and $A_4$ is independently a covalent bond, a substituted or unsubstituted $C_1$-$C_5$ alkylene group, a carbonyl group, or a sulfinyl group, wherein both $A_1$ and $A_2$ are not a covalent bond and both $A_3$ and $A_4$ are not a covalent bond.

2. The lithium battery as claimed in claim 1, wherein at least one of $A_1$, $A_2$, $A_3$, and $A_4$ is an unsubstituted or substituted $C_1$-$C_5$ alkylene group, wherein a substituent of the substituted $C_1$-$C_5$ alkylene group is at least one selected from a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, a halogen-substituted or unsubstituted $C_2$-$C_{40}$ heteroaryl group, or a polar functional group having at least one heteroatom.

3. The lithium battery as claimed in claim 2, wherein the substituted $C_1$-$C_5$ alkylene group is substituted with a polar functional group including at least one heteroatom, wherein the polar functional group is —F, —Cl, —Br, —I, —C(═O)OR$^{16}$, —OR$^{16}$, —OC(═O)OR$^{16}$, —R$^{15}$OC(═O)OR$^{16}$, —C(═O)R$^{16}$, —R$^{15}$C (═O)R$^{16}$, —OC(═O)R$^{16}$, —R$^{15}$OC(═O)R$^{16}$, —C(═O)—O—C(═O)R$^{16}$, —R$^{15}$C(═O)—O—C(═O)R$^{16}$, -SR$^{16}$, —R$^{15}$SR$^{16}$, —SSR$^{16}$, —R$^{15}$SSR$^{16}$, -S(═O)R$^{16}$, —R$^{15}$S(═O)R$^{16}$, —R$^{15}$C(═S)R$^{16}$, —R$^{15}$C(═S) SR$^{16}$, —R$^{15}$SO$_3$R$^{16}$, —SO$_3$R$^{16}$, —NNC(═S)R$^{16}$, —R$^{15}$NNC(═S)R$^{16}$, —R$^{15}$N═C═S, —NCO, —R$^{15}$—NCO, —NO$_2$, —R$^{15}$NO$_2$, —R$^{15}$SO$_2$R$^{16}$, —SO$_2$R 16,

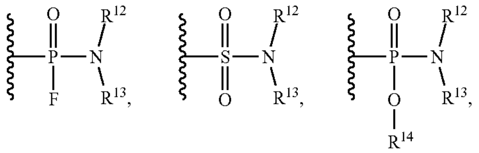

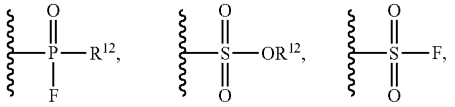

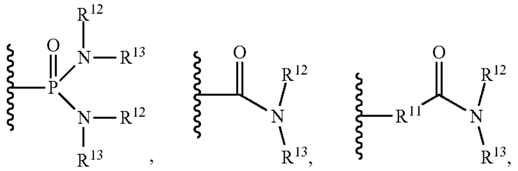

,

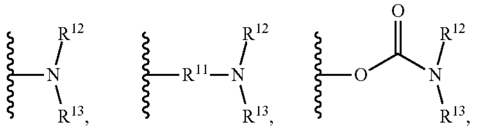

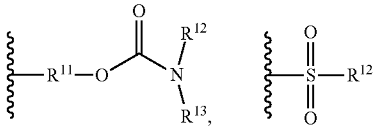

,

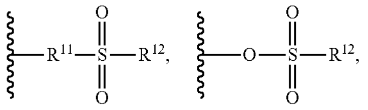

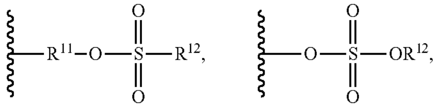

-continued

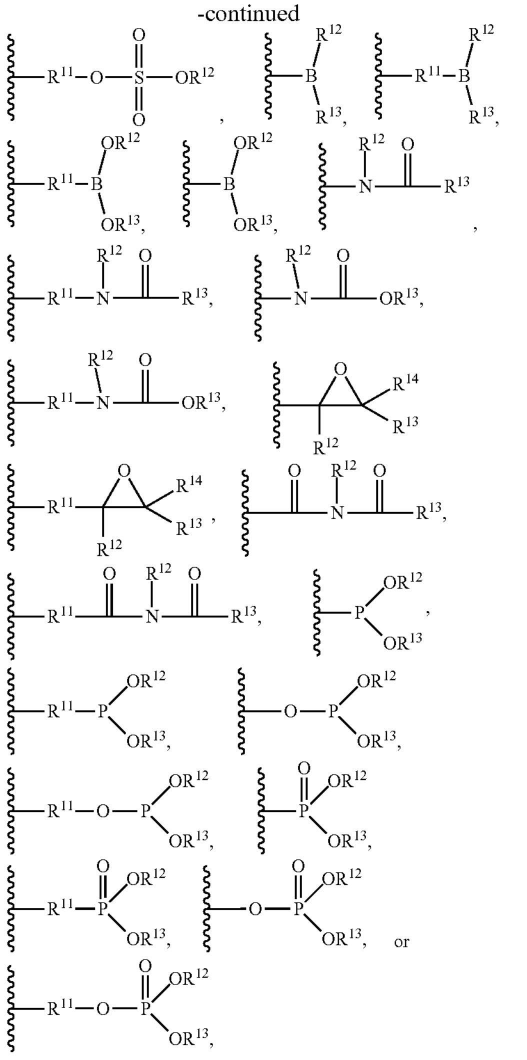

wherein, in the formulae above, each of $R^{11}$ and $R^{15}$ is independently a halogen-substituted or unsubstituted $C_1$-$C_{20}$ alkylene group, a halogen-substituted or unsubstituted $C_2$-$C_{20}$ alkenylene group, a halogen-substituted or unsubstituted $C_2$-$C_{20}$ alkynylene group, a halogen-substituted or unsubstituted $C_3$-$C_{12}$ cycloalkylene group, a halogen-substituted or unsubstituted $C_6$-$C_{40}$ arylene group, a halogen-substituted or unsubstituted $C_2$-$C_{40}$ heteroarylene group, a halogen-substituted or unsubstituted $C_7$-$C_{15}$ alkylarylene group, or a halogen-substituted or unsubstituted $C_7$-$C_{15}$ aralkylene group; and each of $R^{12}$, $R^{13}$, $R^{14}$ and $R^{16}$ is independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{12}$ cycloalkyl group, a halogen-substituted or unsubstituted $C_6$-$C_{40}$ aryl group, a halogen-substituted or unsubstituted $C_2$-$C_{40}$ heteroaryl group, a halogen-substituted or unsubstituted $C_7$-$C_{15}$ alkylaryl group, a halogen-substituted or unsubstituted $C_7$-$C_{15}$ trialkylsilyl group, or a halogen-substituted or unsubstituted $C_7$-$C_{15}$ aralkyl group.

4. The lithium battery as claimed in claim 1, wherein at least one of $A_1$, $A_2$, $A_3$, and $A_4$ is an unsubstituted or substituted $C_1$-$C_5$ alkylene group, wherein a substituent of the substituted $C_1$-$C_5$ alkylene group is a halogen, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

5. The lithium battery as claimed in claim 1, wherein:

the bicyclic sulfate-based compound represented by Formula 1 is represented by Formula 2 or 3:

<Formula 2>

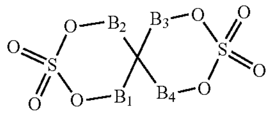

<Formula 3>

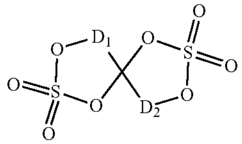

in Formulae 2 and 3, each of $B_1$, $B_2$, $B_3$, $B_4$, D1, and D2 is independently $-C(E_1)(E_2)-$, a carbonyl group, or a sulfinyl group; and each of $E_1$ and $E_2$ is independently hydrogen, a halogen, a halogen-substituted or unsubstituted $C_1$-$C_{20}$ alkyl group, a halogen-substituted or unsubstituted $C_2$-$C_{20}$ alkenyl group, a halogen-substituted or unsubstituted $C_2$-$C_{20}$ alkynyl group, a halogen-substituted or unsubstituted $C_3$-$C_{20}$ cycloalkenyl group, a halogen-substituted or unsubstituted $C_3$-$C_{20}$ heterocyclic group, a halogen-substituted or unsubstituted $C_6$-$C_{40}$ aryl group, or a halogen-substituted or unsubstituted $C_2$-$C_{40}$ heteroaryl group.

6. The lithium battery as claimed in claim 5, wherein each of $E_1$ and $E_2$ is independently hydrogen, a halogen, a halogen-substituted or unsubstituted $C_1$-$C_{10}$ alkyl group, a halogen-substituted or unsubstituted $C_6$-$C_{40}$ aryl group, or a halogen-substituted or unsubstituted $C_2$-$C_{40}$ heteroaryl group.

7. The lithium battery as claimed in claim 5, wherein each of $E_1$ and $E_2$ is independently hydrogen, fluorine (F), chlorine ($C_1$), bromine (Br), iodine (I), a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

8. The lithium battery as claimed in claim 1, wherein the bicyclic sulfate-based compound represented by Formula 1 is represented by Formula 4 or 5:

<Formula 4>

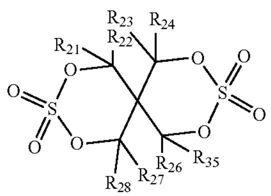

-continued

<Formula 5>

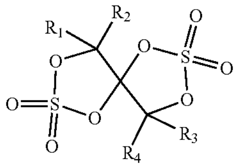

wherein, in Formulae 4 and 5, each of $R^1$, $R^2$, $R^3$, $R^4$, $R^{21}$, $R^{22}$, $R^{23}$, $R^{24}$, $R^{25}$, $R^{26}$, $R^{27}$, and $R^{28}$ is independently hydrogen, a halogen, a halogen-substituted or unsubstituted $C_1$-$C_{20}$ alkyl group, a halogen-substituted or unsubstituted $C_6$-$C_{40}$ aryl group, or a halogen-substituted or unsubstituted $C_2$-$C_{40}$ heteroaryl group.

9. The lithium battery as claimed in claim 8, wherein each of $R^1$, $R^2$, $R^3$, $R^4$, $R^{21}$, $R^{22}$, $R^{23}$, $R^{24}$, $R^{25}$, $R^{26}$, $R^{27}$, and $R^{28}$ is independently hydrogen, F, Cl, Br, I, a methyl group, an ethyl group, a propyl group, an isopropyl group, a butyl group, a tert-butyl group, a trifluoromethyl group, a tetrafluoroethyl group, a phenyl group, a naphthyl group, a tetrafluorophenyl group, a pyrrolyl group, or a pyridinyl group.

10. The lithium battery as claimed in claim 1, wherein the bicyclic sulfate-based compound represented by Formula 1 is represented by one of Formulae 6 to 17 below:

<Formula 6>

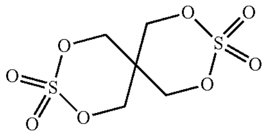

<Formula 7>

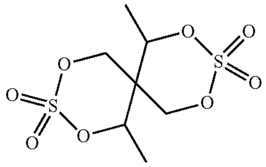

<Formula 8>

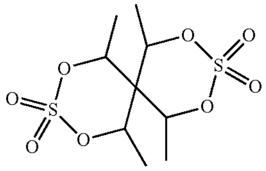

<Formula 9>

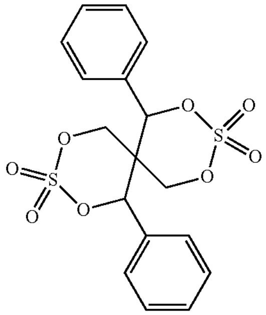

-continued

<Formula 10>

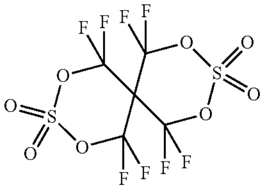

<Formula 11>

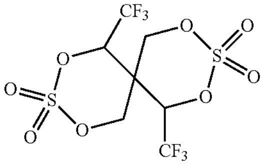

<Formula 12>

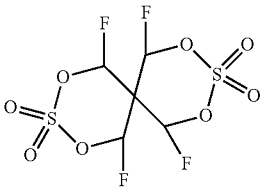

<Formula 13>

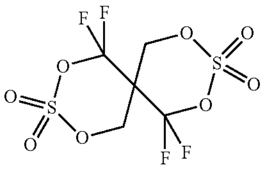

<Formula 14>

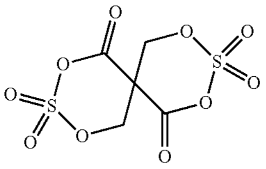

<Formula 15>

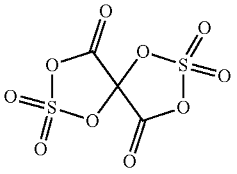

<Formula 16>

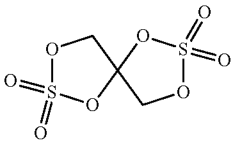

<Formula 17>

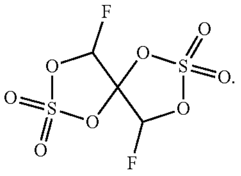

11. The lithium battery as claimed in claim 1, wherein the first lithium salt in the organic electrolytic solution includes $LiPF_6$, $LiBF_4$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlC_{14}$, $LiN(C_xF_{2x+1}SO_2)$ $(C_yF_{2y+1}SO_2)$ where $2 \leq x \leq 20$ and $2 \leq y \leq 20$, LiCl, or LiI.

12. The lithium battery as claimed in claim 1, wherein:

the organic electrolytic solution further includes a cyclic carbonate compound, wherein the cyclic carbonate compound is selected from vinylene carbonate (VC), VC substituted with a halogen, a cyano (CN) group, or a nitro ($NO_2$) group, vinylethylene carbonate (VEC), VEC substituted with halogen, CN, or $NO_2$, fluoroethylene carbonate (FEC), or FEC substituted with a halogen, CN, or $NO_2$, and an amount of the cyclic carbonate compound is from about 0.01 wt % to about 5 wt % based on the total weight of the organic electrolytic solution.

13. The lithium battery as claimed in claim 1, wherein:

the organic electrolytic solution further includes a second lithium salt different from the first lithium salt and represented by one of Formulae 18 to 25 below, and <Formula 18>

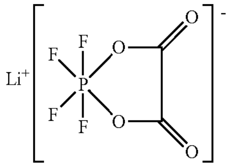

<Formula 19>

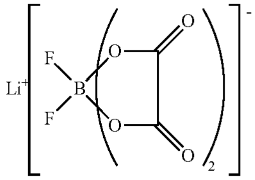

<Formula 20>

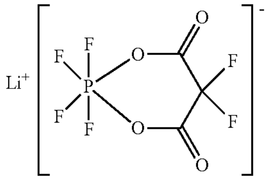

-continued

<Formula 21>

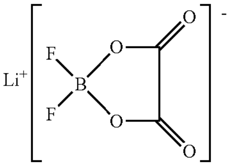

<Formula 22>

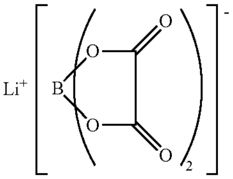

<Formula 23>

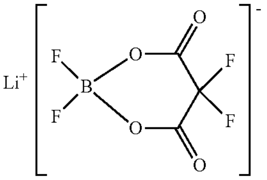

<Formula 24>

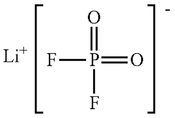

<Formula 25>

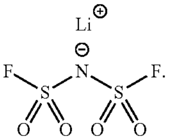

an amount of the second lithium salt is from about 0.1 wt % to about 5 wt % based on the total weight of the organic electrolytic solution.

14. The lithium battery as claimed in claim 1, wherein the first lithium transition metal oxide and the second lithium transition metal oxide have a bimodal particle size distribution.

* * * * *